(12) United States Patent
Masuda

(10) Patent No.: US 8,055,107 B2
(45) Date of Patent: Nov. 8, 2011

(54) OPTICAL ROTARY ADAPTER AND OPTICAL TOMOGRAPHIC IMAGING SYSTEM USING THE SAME

(75) Inventor: Tadashi Masuda, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 617 days.

(21) Appl. No.: 12/239,784

(22) Filed: Sep. 28, 2008

(65) Prior Publication Data

US 2009/0251704 A1    Oct. 8, 2009

(30) Foreign Application Priority Data

Sep. 28, 2007  (JP) .................................. 2007-255785
Jan. 31, 2008  (JP) .................................. 2008-020398

(51) Int. Cl.
    *G02B 6/26*        (2006.01)
(52) U.S. Cl. ............................................... 385/26
(58) Field of Classification Search ................. 385/26
    See application file for complete search history.

(56) References Cited

U.S. PATENT DOCUMENTS

| | | | | |
|---|---|---|---|---|
| 6,069,698 A * | 5/2000 | Ozawa et al. ................. | 356/511 |
| 6,687,010 B1 * | 2/2004 | Horii et al. .................... | 356/479 |
| 7,133,138 B2 * | 11/2006 | Horii et al. .................... | 356/497 |
| 7,180,600 B2 * | 2/2007 | Horii et al. .................... | 356/479 |
| 7,633,623 B2 * | 12/2009 | Hatori ............................. | 356/450 |
| 2010/0228124 A1 * | 9/2010 | Brennan et al. ................ | 600/437 |
| 2010/0228132 A1 * | 9/2010 | Brennan et al. ................ | 600/478 |
| 2010/0228238 A1 * | 9/2010 | Brennan et al. ................. | 606/13 |

FOREIGN PATENT DOCUMENTS

JP          2000-131222 A         5/2000

* cited by examiner

*Primary Examiner* — Sung Pak
(74) *Attorney, Agent, or Firm* — Sughrue Mion, PLLC

(57) ABSTRACT

The optical rotary adapter is used with an optical tomographic imaging system for acquiring an optical tomographic image of an object under measurement. The adapter includes a fixed sleeve, a stationary optical fiber supported by the fixed sleeve and having an inclined end face, a stationary collimating lens spaced a given distance from the inclined end face, a mounting cylinder carried rotatably with respect to the fixed sleeve, a rotary optical fiber mounted to the mounting cylinder and having an inclined end face, a rotary collimating lens mounted to the mounting cylinder and disposed with a given distance from the inclined end face, and a rotation actuating device for rotating said mounting cylinder. The central axes of the stationary and rotary optical fibers are offset from or inclined with respect to a central axis of rotation of the mounting cylinder to reduce attenuation of returning light from the object.

19 Claims, 8 Drawing Sheets

OPTICAL ROTARY ADAPTER AND OPTICAL TOMOGRAPHIC IMAGING SYSTEM USING THE SAME

BACKGROUND OF THE INVENTION

The present invention relates to an optical rotary adapter and an optical tomographic imaging system using the same and more specifically to an optical rotary adapter that provides rotatable connection between optical fibers for guiding measuring light to the object under measurement and guiding returning light from the object under measurement to acquire an optical tomographic image of the object under measurement and an optical tomographic imaging system that irradiates the object under measurement with light and acquires a tomographic image from the light reflected by and returned from the object under measurement.

Acquisition of a cross-sectional image of a sample under measurement such as biological tissue without cutting thereinto may be achieved using an optical tomographic imaging system employing optical coherence tomography (OCT) measuring.

The OCT measuring is a kind of optical interferometric measurement using the optical interference that occurs only when the optical path lengths of the measuring light and the reference light, into which the light from the light source is divided, are matched to within the coherence length of the light from the light source.

An optical tomographic imaging system using the OCT measuring is disclosed, for example, in JP 2000-131222 A, which comprises a light source; a first optical coupler for splitting the light emitted from the light source into measuring light and reference light; an optical scan probe including a measuring unit for irradiating the sample under test or the object under measurement with the measuring light and detecting the light reflected and returned therefrom, an optical fiber for transmitting the measuring light and the returning light, and a transparent sheath covering the optical fiber and the measuring unit; and a second coupler for causing the reference light to interfere with the returning light both guided along the same optical path length as the measuring light; and an optical tomography system including a computing unit for detecting a tomographic image from the results of interference. With the optical tomographic imaging system disclosed in JP 2000-131222 A, which has the optical fiber in the measuring unit rotatably connected to an optical rotary joint, the measuring unit located close to the tip of the optical scan probe is inserted up to a position to be measured and rotated by turning the optical fiber to acquire a plurality of tomographic images of the object under measurement with its rotating measuring unit, thus reconstructing a two-dimensional sectional image.

In the optical rotary joint disclosed in JP 2000-131222 A, a rotor into which the rotary optical fiber is inserted along its axis is fitted into the socket of a rotor receiver into which the stationary optical fiber is inserted along its axis such that the rotor receiver rotatably supports the rotor by the intermediate of bearings. The rotor is turned at a constant speed via a belt. Convex lenses are disposed on one end of the rotary optical fiber and one end of the stationary optical fiber opposite each other to permit efficient optical transmission between the stationary optical fiber, not rotatable, and the rotary optical fiber, adapted to be rotatable.

SUMMARY OF THE INVENTION

The optical rotary joint used in the optical tomographic imaging system disclosed in JP 2000-131222 A has the convex lenses disposed on the opposite ends of the optical fibers, as described above, such that the optical fibers are not in contact with each other. Accordingly, one of these optical fibers is rotatable with respect to the other and the rotor, in which the rotary optical fiber leading to the optical scan probe is inserted and the rotor receiver, in which the stationary optical fiber is inserted, are detachable from each other to permit washing of the optical scan probe that was inserted into part of a body such as a bodily cavity. Thus, the ends of the optical fibers can be protected from break or damage when removing the rotor from the rotor receiver. Further, the convex lenses thus disposed allow the light delivered through one of the optical fibers to be focused and then enter the other optical fiber, achieving optical transmission with a certain level of efficiency.

In the optical rotary joint disclosed in JP 2000-131222 A, however, no consideration is given to the decrease of the signal-to-noise ratio of the returning light from the object under measurement caused by the attenuation as light is reflected and refracted at the opposite ends of the optical fibers. In the optical tomographic imaging system, the amount of the returning light from the object under measurement should be at least about $10^{-6}$ to $10^{-10}$ in relation to the amount of the measuring light after the measuring light attenuates at the opposite end faces of both optical fibers. Accordingly, the attenuation of the returning light and the decrease of the signal-to-noise ratio thereof occurring at the opposite ends of the connected optical fibers as light is reflected at the end faces were a matter of great importance. However, such a problem was not addressed in the optical rotary joint disclosed in JP 2000-131222 A in any manner.

A first object of the invention is to eliminate the above problem associated with the prior art and provide an optical rotary adapter wherein the optical fibers guiding the measuring light to the object under measurement and guiding the returning light from the object under measurement are rotatably and detachably connected, wherein the connecting ends of the optical fibers can be protected from break or damage when attaching or detaching the optical fibers, and wherein the attenuation of the returning light from the object under measurement and the decrease of the signal-to-noise ratio thereof occurring at the opposite ends of the connected optical fibers as light is reflected at the end faces can be prevented.

A second object of the invention is to provide an optical tomographic imaging system capable of efficiently acquiring a high-resolution tomographic image of the object under measurement by using the optical rotary adapter capable of achieving said first object.

A first aspect of the invention to achieve the above first object is to provide an optical rotary adapter used with an optical tomographic imaging system for acquiring an optical tomographic image of an object under measurement, the optical rotary adapter rotatably connecting optical fibers guiding measuring light to the object under measurement and guiding reflected returning light from the object under measurement, the optical rotary adapter comprising a fixed sleeve, a stationary optical fiber fixedly supported by the fixed sleeve and having on one end thereof an inclined end face inclined a given angle with respect to a plane perpendicular to a central axis of the stationary optical fiber, a stationary collimating lens spaced a given distance from the inclined end face of the optical fiber, a mounting cylinder carried rotatably with respect to the fixed sleeve, a rotary optical fiber fixedly mounted to the mounting cylinder so as to be disposed opposite the stationary collimating lens and having an inclined end face inclined a given angle with respect to a plane perpendicular to a central axis of the rotary optical fiber, a rotary collimating lens fixedly mounted to the mounting cylinder and disposed between the stationary collimating lens and the rotary optical fiber with a given distance from the inclined end face of the rotary optical fiber, and rotation actuating means for rotating the mounting cylinder, wherein the central axes of the stationary optical fiber and the rotary optical fiber are offset from or inclined with respect to a central axis of rotation of the mounting cylinder to reduce attenuation of the returning light.

Preferably, the stationary optical fiber is fixedly supported substantially at a center of the fixed sleeve whereas the rotary optical fiber is fixedly supported substantially at a center of the mounting cylinder such that the central axes of the stationary optical fiber and the rotary optical fiber are parallel to and offset from the central axis of rotation of the mounting cylinder to reduce attenuation of the returning light.

Preferably, respective offset amounts $\delta 1$ and $\delta 2$ between the central axes of the stationary optical fiber and the rotary optical fiber with respect to the central axis of rotation of the mounting cylinder satisfy following expressions (1), (2), (3) and (4):

$$n1 \times \sin\theta 1 = n3 \times \sin\theta 3 \tag{1}$$

$$\delta 1 = f1 \times \tan(\theta 3 - \theta 1) \tag{2}$$

$$n2 \times \sin\theta 2 = n3 \times \sin\theta 4 \tag{3}$$

$$\delta 2 = f2 \times \tan(\theta 4 - \theta 2) \tag{4}$$

where $\theta 1$ and $\theta 2$ are inclination angles respectively of the inclined end faces of the stationary optical fiber and the rotary optical fiber with respect to planes perpendicular to the central axes of the optical fibers; n1 and n2 are refractive indices respectively of the stationary optical fiber and the rotary optical fiber; n3 is refractive index of a medium between the stationary optical fiber and the rotary optical fiber propagating light; $\theta 3$ and $\theta 4$ are angles of light traveling inside the optical fibers in a direction parallel to the central axes of the optical fibers and refracted at interfaces between the inclined end faces of the optical fibers and the medium with respect to respective normal lines to the inclined end faces; and f1 and f2 are focal distances, respectively, of the stationary collimating lens and the rotary collimating lens, the focal distances being equal respectively to distances along the optical axes between respective centers of the inclined end faces of the stationary optical fiber and the rotary optical fiber on the one hand and respective centers of the stationary collimating lens and the rotary collimating lens on the other hand assuming that the collimating lenses are thin sheet lenses.

Preferably, the stationary optical fiber and the rotary optical fiber are supported by ferrules, respectively, and the ferrules have their respective inclined end faces sharing same planes respectively with the inclined end faces of the stationary optical fiber and the rotary optical fiber.

Preferably, the stationary optical fiber and the rotary optical fiber are supported at the center of their respective ferrules held by respective holders fixedly mounted to the fixed sleeve and the mounting cylinder, respectively, such that the central axes of the stationary optical fiber and the rotary optical fiber are in an offset position from the central axis of rotation of the mounting cylinder by offsetting the ferrules respectively supporting the stationary optical fiber and the rotary optical fiber.

Preferably, the stationary optical fiber and the rotary optical fiber are disposed such that the centers of their respective inclined end faces lie on the central axis of rotation, wherein the stationary collimating lens and the rotary collimating lens are disposed such that their respective centers lie on the central axis of rotation, wherein the stationary optical fiber is fixedly supported by the fixed sleeve at a given inclination angle while the rotary optical fiber is fixedly mounted to the mounting cylinder at a given inclination angle, and wherein the central axes of the stationary optical fiber and the rotary optical fiber are each inclined with respect to the central axis of rotation of the mounting cylinder to reduce attenuation of the returning light.

Preferably, inclination angles $\phi 1$ and $\phi 2$ between the central axes of the stationary optical fiber and the rotary optical fiber, respectively, with respect to the central axis of rotation of the mounting cylinder satisfy following expressions (5), (6), (7) and (8):

$$n1 \times \sin\theta 1 = n3 \times \sin\theta 3 \tag{5}$$

$$\phi 1 = \theta 3 - \theta 1 \tag{6}$$

$$n2 \times \sin\theta 2 = n3 \times \sin\theta 4 \tag{7}$$

$$\phi 2 = \theta 4 - \theta 2 \tag{8}$$

where $\theta 1$ and $\theta 2$ are inclination angles of the inclined end faces of the stationary optical fiber and the rotary optical fiber, respectively, with respect to planes perpendicular to the central axes of the optical fibers; n1 and n2 are refractive indices, respectively, of the stationary optical fiber and the rotary optical fiber; n3 is refractive index of a medium between the stationary optical fiber and the rotary optical fiber propagating light; and $\theta 3$ and $\theta 4$ are angles of light traveling inside the optical fibers in a direction parallel to the central axes of the optical fibers and refracted at interfaces respectively between the inclined end faces of the optical fibers and the medium with respect to normal lines to the respective end faces of the stationary optical fiber and the rotary optical fiber.

Preferably, the stationary optical fiber and the rotary optical fiber are supported by ferrules, respectively, and the ferrules have their respective inclined end faces sharing same planes respectively with the inclined end faces of the stationary optical fiber and the rotary optical fiber.

Preferably, the stationary optical fiber and the rotary optical fiber are supported at the center of their respective ferrules held by respective holders fixedly mounted to the fixed sleeve and the mounting cylinder, respectively, such that the central axes of the stationary optical fiber and the rotary optical fiber are inclined with respect to the central axis of rotation of the mounting cylinder by inclining the ferrules supporting the stationary optical fiber and the rotary optical fiber, respectively.

Preferably, the stationary optical fiber and the stationary collimating lens on the one hand and the rotary optical fiber and the rotary collimating lens on the other hand are disposed so as to become symmetric as the rotary optical fiber and the rotary collimating lens rotate.

Preferably, the mounting cylinder fixedly supporting the rotary optical fiber and the rotary collimating lens are removable from the fixed sleeve fixedly supporting the rotary optical fiber and the rotary collimating lens.

Preferably, the optical rotary adapter further comprises a rotary cylinder having one end thereof attached to the mounting cylinder and rotating about the central axis of rotation unitarily with the mounting cylinder, wherein the inclined end face of one end of the rotary optical fiber is attached to the mounting cylinder such that the central axis of the rotary optical fiber is offset or inclined with respect to the central axis of rotation of the mounting cylinder, and the rotary optical fiber is supported by the rotary cylinder at the other end of the rotary cylinder.

Preferably, the rotary optical fiber is supported at the other end of the rotary cylinder at a center of the rotary cylinder such that the central axis of the rotary optical fiber coincides with the central axis of rotation of the mounting cylinder.

Preferably, the rotary optical fiber has the other end face at the other end of the rotary cylinder, the other end of the rotary cylinder forming a terminal for a fixed type optical connector.

Preferably, the other end face of the rotary optical fiber is supported at a center of the rotary cylinder such that the central axis of the rotary optical fiber coincides with the central axis of rotation of the mounting cylinder.

Preferably, the rotary optical fiber extends from the other end of the rotary cylinder and has a tip connected to a measuring unit for irradiating the object under measurement with the measuring light and acquiring returning light from the object under measurement, the rotary optical fiber being rotatably held in a transparent probe sheath to form part of an optical probe.

A second aspect of the invention to solve the above problems and to achieve the second object of the invention is to provide an optical tomographic imaging system comprising a main body of system for acquiring an optical tomographic image of an object under measuring; an optical probe including a rotary optical fiber for guiding measuring light from the main body of the system to the object under measurement and guiding returning light from the object under measurement, a measuring unit disposed at a tip of the rotary optical fiber for irradiating the object under measurement with the measuring light and acquiring returning light from the object under measurement, and a probe sheath covering the periphery of the rotary optical fiber and the measuring unit so as to rotatably hold the rotary optical fiber and the measuring unit and having at least a region thereof formed of a transparent material transmitting the measuring light from the measuring unit and the returning light from the object under measurement; a stationary optical fiber connected with the main body of the system for guiding the measuring light to the rotary optical fiber and guiding the returning light guided by the rotary optical fiber to the main body of the system; and the optical rotary adapter according to the first aspect of the invention for rotatably connecting the rotary optical fiber to the stationary optical fiber to transmit the measuring light and the returning light; wherein the main body of the system uses the guided returning light to acquire the optical tomographic image of the object under measurement.

Preferably, the main body of the system comprises a light source; a splitter for splitting light emitted from the light source into the measuring light and reference light; a combiner for combining the returning light detected by the measuring unit of the optical probe and guided through the rotary optical fiber, the optical rotary adapter and the stationary optical fiber with the reference light to generate interference light; an interference light detector for detecting the interference light as interference signal; and a tomographic information generator for acquiring the tomographic image from the interference signal detected by the interference light detector.

Preferably, the light source emits light as it sweeps a wavelength with a constant period.

According to the first aspect of the invention directed to the optical rotary adapter, the optical fibers guiding the measuring light to the object under measurement and guiding the returning light from the object under measurement are rotatably and, preferably, detachably connected, the connecting ends of the optical fibers can be protected from break or damage when attaching or detaching the optical fibers, and the attenuation of the returning light from the object under measurement and the decrease of the signal-to-noise ratio thereof occurring at the opposite ends of the connected optical fibers as light is reflected at the end faces can be prevented.

A second aspect of the invention directed to the optical tomographic imaging system achieves efficient acquisition of a high-resolution tomographic image of the object under measurement by using the optical rotary adapter according to the first aspect capable of producing said effect.

BRIEF DESCRIPTION OF THE DRAWINGS

These and other objects, features, and advantages of the present invention will be apparent from the following detailed description and accompanying drawings in which.

DETAILED DESCRIPTION OF THE INVENTION

Now, the inventive optical rotary adapter and the optical tomographic imaging system using the same will be described in detail referring to the embodiments illustrated in the attached drawings.

Figure 1:
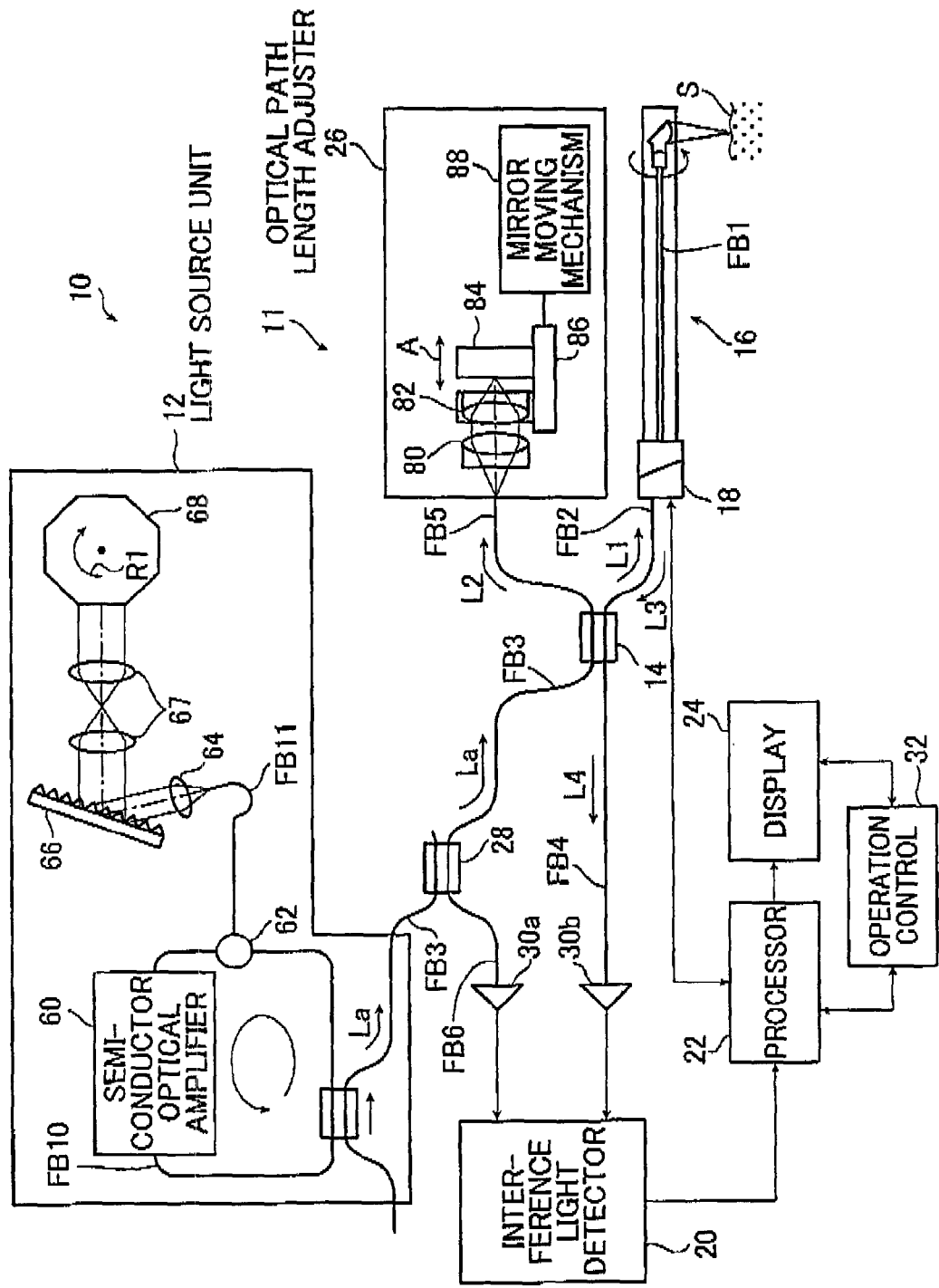
FIG. 1 is a block diagram schematically illustrating a configuration of an embodiment of the inventive optical tomographic imaging system using the inventive optical rotary adapter.

FIG. 1 is a block diagram illustrating a schematic configuration of an embodiment of the inventive optical tomographic imaging system using the inventive optical rotary adapter.

An optical tomographic imaging system 10 according to the invention illustrated in FIG. 1 acquires a tomographic image of an object under measurement by a measuring method based upon optical coherence tomography or OCT. The optical tomographic imaging system 10 comprises:

a main body of the system 11 including a light source unit 12 for emitting light La, a splitter/combiner 14 for splitting the light La emitted by the light source unit 12 into measuring light L1 and reference light L2 and combining returning light L3 from the object under measurement or the sample under test and the reference light L2 to produce interference light L4, an interference light detector 20 for detecting the interference light L4 produced by the splitter/combiner 14 as interference signal, a processor 22 for processing the interference signal detected by the interference light detector 20 to acquire an optical tomographic image (also referred to simply as "tomographic image" below), and a display 24 for displaying the tomographic image acquired by the processor 22;

an optical probe 16 having a rotary optical fiber FB1 for guiding the measuring light L1 split by the splitter/combiner 14 of the main body of the system 11 to the object under measurement and for guiding the returning light L3 from the object under measurement;

a stationary optical fiber FB2 for guiding the measuring light L1 to the rotary optical fiber FB1 and guiding the returning light L3 guided by the rotary optical fiber FB1; and an optical rotary adapter 18 of the invention for rotatably connecting the rotary optical fiber FB1 to the stationary optical fiber FB2 to transmit the measuring light L1 and the returning light L3.

The optical tomographic imaging system 10 further comprises in the main body of the system 11 an optical path length adjuster 26 for adjusting the optical path length of the reference light L2, an optical fiber coupler 28 for splitting the light La emitted by the light source unit 12, a detector 30a for detecting the reference light L2 and a detector 30b for detecting the returning light L3, an operation control 32 for entering various conditions in the processor 22, the display 24, etc., and changing the settings, among other functions. In the optical tomographic imaging system 10 illustrated in FIG. 1, various light beams such as the emitted light La, the measuring light L1, the reference light L2, and the returning light L3 as described above are guided between the components such as optical devices, using various optical fibers FB (FB3, FB4, FB5, FB6, etc.) including the rotary optical fiber FB1 and the stationary optical fiber FB2 as optical transmission paths, as will be described later in detail.

The splitter/combiner 14, the interference light detector 20, the optical path length adjuster 26, the optical fiber coupler 28, and the detectors 30a and 30b constitute an interferometer.

First, the optical rotary adapter of the invention used for the optical tomographic imaging system 10 illustrated in FIG. 1 will be described.

Figure 2:
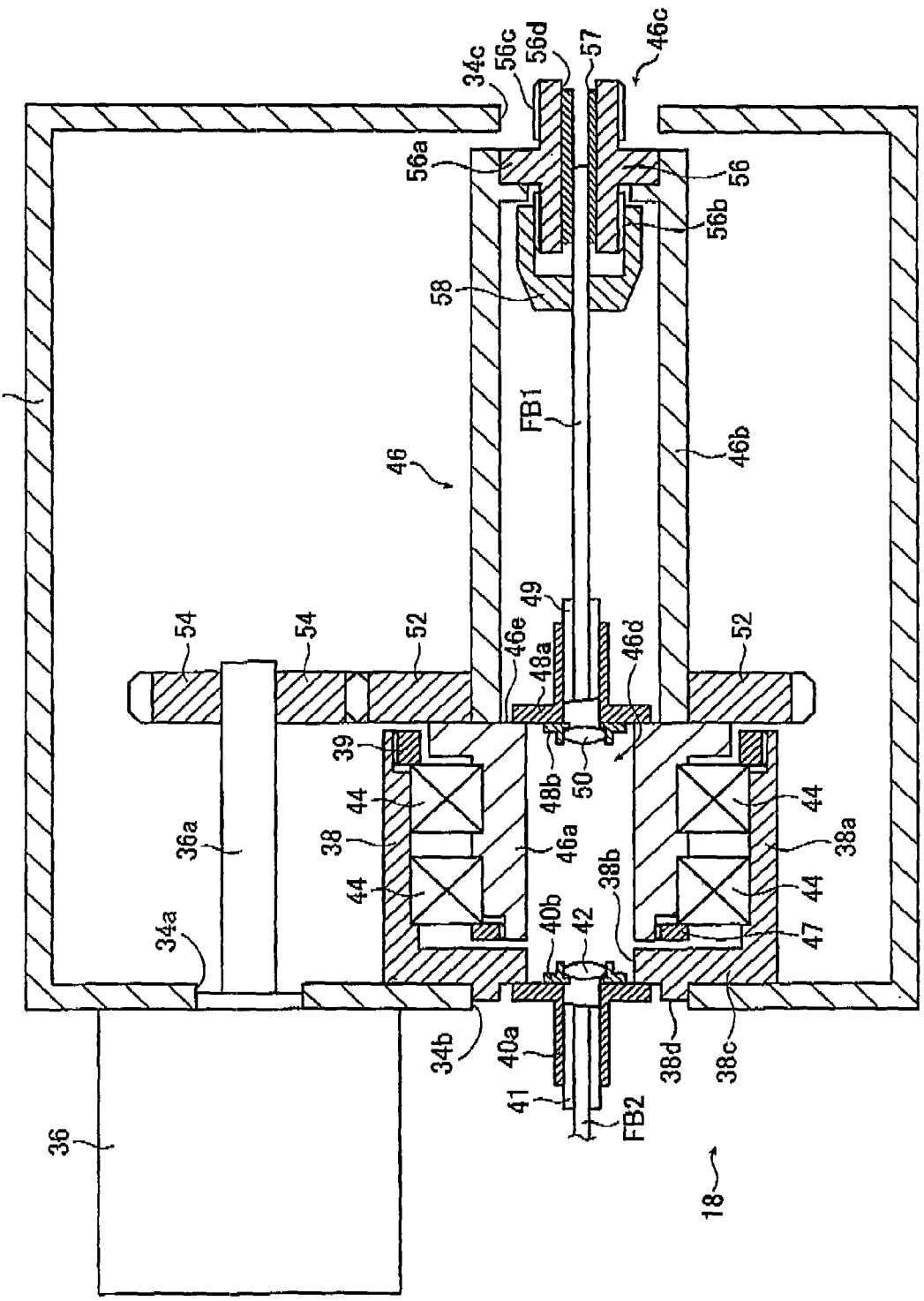
FIG. 2 is a schematic sectional view of an embodiment of the optical rotary adapter illustrated in FIG. 1.
Figure 3:
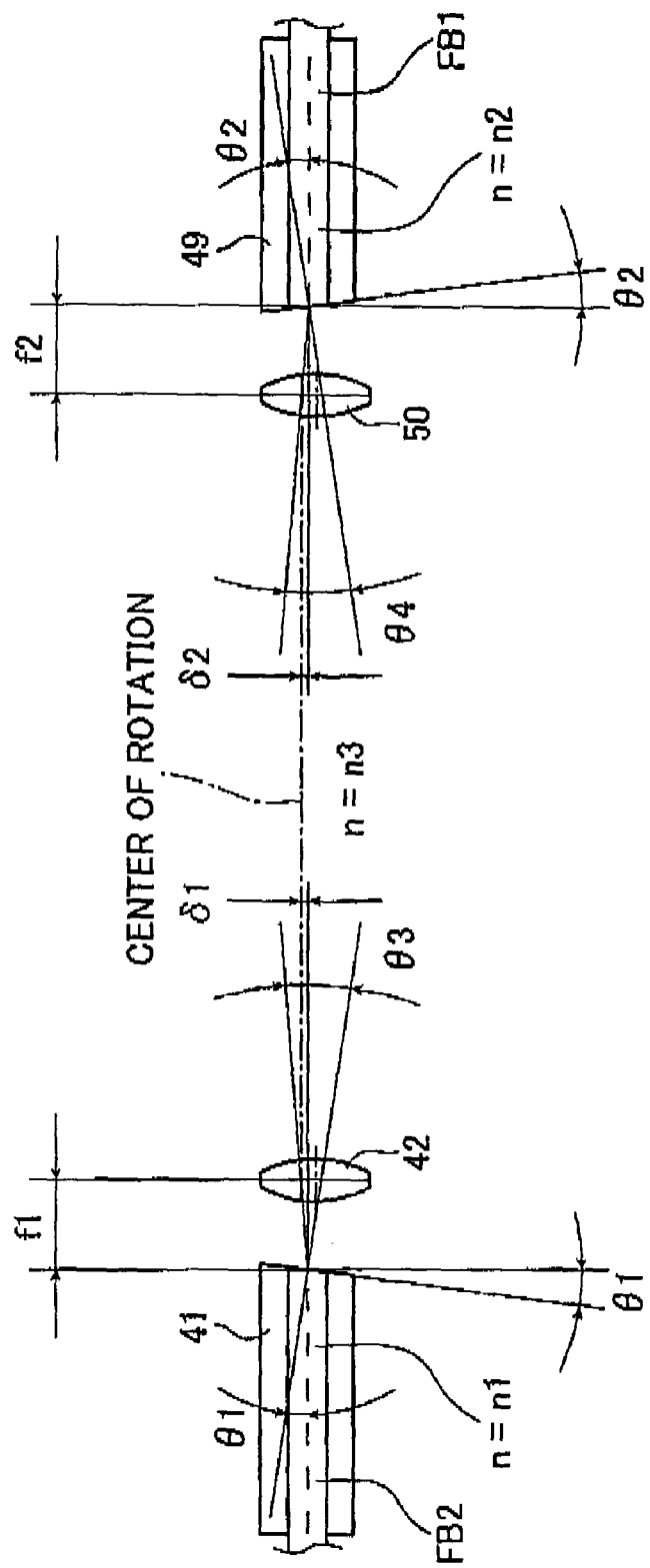
FIG. 3 is a view for explaining an example of the positional relationship of the optical fibers and the collimating lenses with respect to the center of rotation of the optical rotary adapter illustrated in FIG. 2.

FIG. 2 is a schematic sectional view of an embodiment of the inventive optical rotary adapter illustrated in FIG. 1; FIG. 3 is a view for explaining an example of the positional relationship of optical fibers and collimating lenses with respect to the center of rotation of the optical rotary adapter illustrated in FIG. 2.

The optical rotary adapter 18 illustrated in FIG. 2 comprises a casing 34, a motor 36 mounted on the outside of the casing 34, a fixed sleeve 38 secured inside the casing 34, the stationary optical fiber FB2 and a stationary collimating lens 42 secured respectively via holders 40a and 40b that in turn are fixedly attached to one end face of the fixed sleeve 38, a rotary assembly 46 essentially composed of a mounting cylinder 46a rotatably carried by the fixed sleeve 38 by the intermediate of bearings 44 and a rotary assembly 46b integrated with the mounting cylinder 46a, the rotary optical fiber FB1 and a rotary collimating lens 50 secured respectively via holders 48a and 48b fixedly mounted at substantially the center of one end face of the mounting cylinder 46a, a gear 52 mounted on the periphery of the rotary cylinder 46b of the rotary assembly 46, and a gear 54 attached to a rotary shaft 36a of the motor 36 and meshing with the gear 52 of the rotary cylinder 46b.

The casing 34 houses components of the optical rotary adapter 18 except the motor 36, the holder 40a, the stationary optical fiber FB2, and some other components. The casing 34 is formed with an aperture 34a through which the rotary shaft 36a of the motor 36 passes; it is further formed with an aperture 34b for mounting the fixed sleeve 38 serving to secure the holder 40a holding the optical fiber FB2 and an aperture 34c allowing the optical fiber FB1 to pass rotatably therethrough. The aperture 34b and the aperture 34c are located opposite each other.

The motor 36 turns the rotary cylinder 46b to rotate the mounting cylinder 46a of the rotary assembly 46, thereby turning the FB1 carried substantially at the center of the mounting cylinder 46a and the rotary cylinder 46b. The motor 36 turns its rotary shaft 36a to rotate the gear 54 mounted at the tip of the rotary shaft 36a, the gear 52 of the rotary cylinder 46b meshing with the gear 54, and the rotary cylinder 46b, thus turning the mounting cylinder 46a of the rotary assembly 46. This causes the FB1 carried substantially at the center of the mounting cylinder 46a and the rotary cylinder 46b of the rotary assembly 46 to rotate.

The fixed sleeve 38 supports the stationary optical fiber FB2 and the stationary collimating lens 42 at their respective given locations and rotatably carries the mounting cylinder 46a of the rotary assembly 46. The fixed sleeve 38 is cylindrical and has a circular tubing section 38a opening on one end thereof and a discal section 38c having a central aperture 38b on the other end. The discal section 38c is attached to the inner wall of the casing 34 such that an annular ridge 38d formed on the outer face of the discal section 38c is fitted in the aperture 34b of the casing 34.

A flange section of the holder 40a is attached to the outside of the discal section 38c of the fixed sleeve 38 thus secured to the casing 34 in such a manner as to cover the central aperture 38b of the fixed sleeve 38.

The mounting cylinder 46a of the rotary assembly 46 is fitted in the circular tubing section 38a of the fixed sleeve 38 from the opening side thereof inwardly with two bearings 44 provided between the inner periphery of the circular tubing section 38a of the fixed sleeve 38 and the outer periphery of the cylindrical mounting cylinder 46a of the rotary assembly 46. The two bearings 44 are urged to the recess in the inner periphery of the circular tubing section 38a of the fixed sleeve 38 and obstructed by a ring 39 having a male thread section engaging the female thread section formed in the inner periphery of the opening end of the circular tubing section 38a to ensure that the bearings do not escape from the engagement with the inner periphery of the circular tubing section 38a toward the opening side.

The holder 40a is a flanged circular tubing member for holding centrally therein the optical fiber FB2 held by a cylindrical ferrule 41. The optical fiber FB2 held by the ferrule 41 is held by the holder 40a such that its end face is spaced a given distance from the flanged end face of the holder 40a (such that the end face is located a given distance into the through-hole of the straight tubing section of the holder 40a). The holder 40a is attached, directed outwardly, to the external periphery of the central aperture 38b of the discal section 38c of the fixed sleeve 38 such that the central axis of the stationary optical fiber FB2 held by the holder 40a is located substantially at the center of the circular central aperture 38b of the fixed sleeve 38 or, to be more specific, in a position eccentric to the central aperture 38b by a given amount (slightly).

The ferrule 41 has the optical fiber FB2 inserted therein to hold and protect the optical fiber FB2 and may typically be a zirconia ferrule or a metal ferrule formed of a metal such as nickel alloy.

The holder 40b is a flanged circular tubing member fox holding the collimating lens 42 and its flange section is attached to the flange section of the holder 40a such that the center of the end face of the optical fiber FB2 and the center of the collimating lens 42 are spaced from each other on the optical axis thereof by a given distance, specifically by the focal distance of the collimating lens 42.

The central axis of the optical fiber FB2 and the center of the collimating lens 42 are offset from each other to permit horizontal emission of light.

The stationary optical fiber FB2 transmits the measuring light L1 split by the splitter/combiner 14 to the rotary optical fiber FB1 and transmits the returning light L3 guided by the optical fiber FB1. The end face of the optical fiber FB2 and the end face of the ferrule 41 having the optical fiber FB2 inserted therein at the core are inclined end faces forming an identical plane inclined a given angle with respect to the plane perpendicular to the central axis of the optical fiber FB2.

The stationary collimating lens 42 collimates the measuring light L1 emitted from the end of the optical fiber FB2 and allows the collimated light to enter the rotary collimating lens 50 and focuses the returning light L3 collimated and returned from the collimating lens 50, allowing the thus focused light to enter the optical fiber FB2. The end face of the optical fiber FB2 and the collimating lens 42 are positioned such that the center of the inclined end face of the optical fiber FB2 and the center of the collimating lens 42 are spaced from each other on the optical axis thereof by a distance equal to the focal distance of the collimating lens 42.

The rotary assembly 46 has the mounting cylinder 46a provided on the forward end thereof (the left-hand side in FIG. 2) and the rotary cylinder 46b provided on the rear end thereof (the right-hand side in FIG. 2) integrated with each other such that these two components rotate as a single unit about an identical axis of rotation, the mounting cylinder 46a on the forward end being fitted into the circular tubing section 38a of the fixed sleeve 38 and rotatably carried by the fixed sleeve 38 by the intermediate of the two bearings 44. Thus, the rotary assembly 46 rotatably carries the rotary optical fiber FB1 held substantially at the center of the inside of the mounting cylinder 46a and the rotary cylinder 46b to permit rotation of the optical fiber FB1.

The mounting cylinder 46a of the rotary assembly 46 is a cylindrical member having a flanged end face 46e on its rear end whereas its forward end face is located opposite the discal section 38c of the fixed sleeve 38, with the two bearings 44 provided on the outer periphery of the mounting cylinder 46a. The mounting cylinder 46a provides the flanged end face 46e on its rear end for securing the optical fiber FB1 and the collimating lens 50 close to the center thereof and thus functions as a mounting cylinder for the optical fiber and the collimating lens whereas the end face of the rotary cylinder 46b is attached to the periphery of the flanged end face 46e.

In the rotary assembly 46, the two bearings 44 are press-fitted in the outer periphery of the mounting cylinder 46a so as to be urged into their respective recesses and secured by a ring 47 having a female thread section engaging the male thread section formed in the periphery of the opening end of the mounting cylinder 46a to ensure that the bearings do not escape from the engagement with the periphery of the mounting cylinder 46a toward the opening side.

The rotary cylinder 46b has an inner periphery having an inside diameter greater than that of the mounting cylinder 46a and having an outside diameter smaller than that of the flanged end face 46e of the mounting cylinder 46a. The forward end face of the rotary cylinder 46b is attached to the periphery of the flanged end face 46e on the rear end of the mounting cylinder 46a such that both share the same central axis of rotation, thus forming the rotary assembly 46 composed of the rotary cylinder 46b integrated with the mounting cylinder 46a.

There is formed between the mounting cylinder 46a and the rotary cylinder 46b a step by the flanged end face 46e of the mounting cylinder 46a. Against that step is abutted the gear 52 mounted on the periphery of the forward end of the rotary cylinder 46b. As the gear 52 turns, the rotary cylinder 46b rotates, causing the rotary assembly 46 and, hence, the mounting cylinder 46a forming part of the rotary assembly 46, to rotate.

At the rear end of the rotary cylinder 46b, there is provided a connecting unit 46c substantially on the central axis thereof. The connecting unit 46c is provided to support the inclined rear end face of the optical fiber FB1 attached to the mounting cylinder 46a so as to lie substantially on the central axis thereof and connect the optical fiber FB1 thus held inside the rotary cylinder 46b to the optical fiber FB1 in the optical probe 16.

Note that the rotary assembly 46 may be configured such that it may be disassembled into the mounting cylinder 46a and the rotary cylinder 46b by disengaging the forward end face of the rotary cylinder 46b from the flanged rear end face 46e of the mounting cylinder 46a.

The flange section of the holder 48a is attached closer to the center of the flanged rear end face 46e of the mounting cylinder 46a of the rotary assembly 46 in such a manner as to cover the central aperture 46d of the mounting cylinder 46a.

The holder 48a, as is the holder 40a, is a flanged circular tubing member for holding centrally therein the optical fiber FB1 held by a cylindrical ferrule 49. The optical fiber FB1 held by the ferrule 49 is held by the holder 48a such that its forward end face is spaced a given distance from the flanged end face of the holder 48a (such that the forward end face is located a given distance into the through-hole of the straight tubing section of the holder 48a). The holder 48a is attached, directed outwardly, to the periphery of the central aperture 46d of the flanged end face 46e such that the central axis of the rotary optical fiber FB1 held by the holder 48a is located substantially at the center of the central aperture 46d of the mounting cylinder 46a or, to be more specific, in an offset (eccentric) position by a given amount (slightly) from the center of rotation of the mounting cylinder 46a (rotary assembly 46).

The ferrule 49 having the optical fiber FB1 inserted therein at the core has a function to hold and protect the optical fiber FB1 and may, as with the ferrule 41, typically be a zirconia ferrule or a metal ferrule formed of a metal such as nickel alloy.

The holder 48b is, as is the holder 40b, a flanged circular tubing member for holding the collimating lens 50, and its flange section is attached to the flange section of the holder 48a such that the center of the forward end face of the optical fiber FB1 and the center of the collimating lens 50 are spaced from each other on the optical axis thereof by a given distance, specifically by the focal distance of the collimating lens 50.

Note that the central axis of the optical fiber FB1 and the center of the collimating lens 50 are provided in an offset positional relationship permitting horizontal emission of light beam.

The rotary optical fiber FB1 guides the measuring light L1 transmitted from the stationary optical fiber FB2 to the object under measurement and guides and transmits the returning light L3 from the object under measurement to the stationary optical fiber FB2. The forward end face of the optical fiber FB1 and the forward end face of the ferrule 49 having the optical fiber FB1 inserted therein at the core are inclined end faces forming an identical plane inclined a given angle with respect to the plane perpendicular to the central axis of the optical fiber S1.

The stationary collimating lens 50 focuses the measuring light L1 collimated by the collimating lens 42 and allows the focused light to enter the optical fiber FB1; it also collimates the returning light L3 emitted from the forward end of the optical fiber FB1 and allows the thus collimated light to enter the stationary collimating lens 42. The forward end face of the optical fiber FB1 and the collimating lens 50 are positioned such that the center of the inclined end face of the optical fiber FB1 and the center of the collimating lens 42 are spaced from each other on the optical axis by a distance equal to the focal distance of the collimating lens 50.

As described earlier, the connecting unit 46c attached to the rear end face of the rotary cylinder 46b of the rotary assembly 46 is provided to support the inclined rear end face of the optical fiber FB1 attached to the mounting cylinder 46a substantially on the central axis thereof and held substantially on the central axis of the rotary cylinder 46b and connect the optical fiber FB1 held inside the rotary cylinder 46b to the optical fiber FB1 in the optical probe 16.

The connecting unit 46c comprises an end face member 56 and a cap nut 58. The end face member 56 includes a flange section 56a fitted in the rear end face of the rotary cylinder 46b so as to abut against the step formed in the inner periphery thereof, male thread sections 56b and 56c provided on the opposite sides of the flange section 56a, and a central through-hole 56d in which the optical fiber FB1, which is held substantially at the center of the mounting cylinder 46a by the holder 48a by the intermediate of the ferrule 49, is inserted substantially along the central axis of rotation and held in position by the intermediate of a split sleeve 57. The cap nut 58 includes a central opening for passing the optical fiber FB1 therethrough, a female thread section engaging the male thread section 56b of the end face member 56, and a through-hole for passing the optical fiber FB1 that is inserted in the central through-hole 56d. The end face member 56 of the connecting unit 46c, in particular the male thread section 56c, functions as a fiber connector for attaching the optical fiber FB1 in the optical probe 16 to the rotary adapter 18.

While the optical fiber FB1, with its inclined forward end face held by the holder 48a located in the position as shown, is disposed substantially at the center of the mounting cylinder 46a and the rotary cylinder 46b such that the central axis of the optical fiber FB1 and the central axis of rotation of the mounting cylinder 46a are offset from each other by a given amount in the illustrated example, it is preferable that the optical fiber FB1 is supported at the center of the rotary cylinder 46b by the end face member 56 and the cap nut 58 such that in the connecting unit 46c at the rear end, the central axis of the optical fiber FB1 and the central axis of rotation of the rotary cylinder 46b coincide with each other.

The male thread section 56c of the connecting unit 46c of the rotary cylinder 46b is located at the aperture 34c of the casing 34 and serves as a connector to optically connect the optical fiber FB1 in the optical probe 16 to the optical fiber FB1 in the rotary assembly 46. The connecting unit 46c may be coupled with a variety of optical connectors including normal optical connectors such as an SC connector, an FC connector, and optical connectors of physical contact type.

Thus, in the optical tomographic imaging system 10 of the invention, connection and disconnection between the stationary optical fiber FB2 directly connected to the main body of the system 11 with an optical connector such as an FC connector and the optical fiber FB1 encased in the optical probe 16 is achieved preferably by providing the connecting unit 46c of the rotary assembly 46 in the inventive optical rotary adapter 18 as a connecting unit for an optical connector and having an optical connector attached to the terminal of the optical fiber FB1 encased in the optical probe 16 to permit connection and disconnection between the connecting unit 46c and the optical connector attached to the terminal of the optical fiber FB1.

As will be described later herein, the optical fiber FB1 in the optical probe 16 is clothed with a spring or the like to protect the optical fiber FB1 and hold it rotatable with a degree of flexibility.

The optical rotary adapter 18 of the invention permits removal of the rotary assembly 46, with the holder 48a holding the optical fiber FB1 attached, by withdrawing the rotary assembly 46 from the fixed sleeve 38 with the holder 40a holding the optical fiber FB2 attached, by removing, for example, the rotary cylinder 46b of the rotary assembly 46 and the gear 52 to remove the ring 39, although this may not be readily achieved because of the press-fitted bearings 44. In the process, the two bearings 44 are withdrawn from the inner periphery of the fixed sleeve 38 together with the mounting cylinder 46a of the rotary assembly 46.

In this procedure, the collimating lenses 50 and 42 each attached adjacent the end of the respective optical fibers FB1 and FB2 prevent accidental damage or break of the connecting ends of the optical fibers FB1 and FB2.

While the connecting unit 46c of the rotary cylinder 46b of the rotary assembly 46 functions as a connector for the optical fiber according to the configuration of the illustrated example, an alternative configuration may be used where the optical fiber FB1 is only held in position by the holder 48a attached to the mounting cylinder 46a, allowing the optical fiber FB1 thus held to extend all the way through the tip of the optical probe 16.

According to the optical rotary adapter 18 of the invention, the central axes of the optical fibers FB1 and FB2 are offset from the center of rotation of the optical fiber FB1, i.e. the center of rotation of the rotary assembly 46 (mounting cylinder 46a), in order to reduce the attenuation of the returning light L3 from the object under measurement for improved signal-to-noise ratio of the returning light L3. The central axes of the optical fibers FB1 and FB2 and the central axis of rotation of the mounting cylinder 46a may be adapted to coincide with each other.

FIG. 3 is a schematic view illustrating the positional relationship between the stationary optical transmission system composed of the stationary optical fiber FB2 and the stationary collimating lens 42 and the rotary optical transmission system composed of the rotary optical fiber FB1 and the rotary collimating lens 50.

Now, as illustrated in FIG. 3, let $\theta_1$ be the inclination angle of the inclined end face of the stationary optical fiber FB2 with respect to a plane perpendicular to the central axis thereof, $n_1$ the refractive index of the optical fiber FB2, $n_3$ the refractive index of the medium between the optical fibers FB2 and FB1 that propagates the light excluding the collimating lenses 42 and 50, and $\theta_3$ the angle (refracting angle) of the light traveling inside the optical fiber F32 in the direction parallel to the central axis thereof and refracted at the interface between the inclined end face of the optical fiber FB2 and the medium with respect to the normal line to the inclined end face, and suppose that the distance along the optical axis between the center of the inclined end face of the optical fiber FB2 and the center of the collimating lens 42 is equal to the focal distance f1 of the collimating lens 42 on the assumption that the collimating lens 42 is a thin sheet lens. Then, the stationary optical fiber FB2 and the collimating lens 42 are preferably mounted to the mounting cylinder 46a such that the offset amount δ1 between the central axis of the optical fiber FB2 and the central axis of rotation of the rotary assembly 46 (mounting cylinder 46a) satisfies the following expressions (1) and (2).

$$n1 \times \sin\theta 1 = n3 \times \sin\theta 3 \qquad (1)$$

$$\delta 1 = f1 \times \tan(\theta 3 - \theta 1) \qquad (2)$$

Likewise, as illustrated in FIG. 3, let θ2 be the inclination angle of the inclined forward end face of the rotary optical fiber FB1 with respect to the plane perpendicular to the central axis thereof, n2 the refractive index of the optical fiber FB1, n3 the refractive index of the above medium propagating the light, and θ4 the angle (refracting angle) of the light traveling inside the optical fiber FB1 in the direction parallel to the central axis thereof and refracted at the interface between the inclined end face and the medium with respect to the normal line to the inclined end face, and suppose that the distance along the optical axis between the center of the inclined end face of the optical fiber FB1 and the center of the collimating lens 50 is equal to the focal distance f2 of the collimating lens 50 on the assumption that the collimating lens 50 is a thin sheet lens. Then, the rotary optical fiber FB1 and the collimating lens 50 are preferably mounted to the mounting cylinder 46a such that the offset amount 82 between the central axis of the optical fiber FB1 and the central axis of rotation of the rotary assembly 46 (mounting cylinder 46a) satisfies the following expressions (3) and (4).

$$n2 \times \sin\theta 2 = n3 \times \sin\theta 4 \qquad (3)$$

$$\delta 2 = f2 \times \tan(\theta 4 - \theta 2) \qquad (4)$$

As described above, the provision of the stationary optical transmission system composed of the stationary optical fiber FB2 and the stationary collimating lens 42 and the rotary optical transmission system composed of the rotary optical fiber FB1 and the rotary collimating lens 50 illustrated in FIG. 3 lessens the attenuation of the returning light L3 from the object under measurement to reduce white noise and improve the signal-to-noise ratio of the returning light L3.

Preferably, the stationary optical transmission system composed of the stationary optical fiber FB2 and the stationary collimating lens 42 and the rotary optical transmission system composed of the rotary optical fiber FB1 and the rotary collimating lens 50 illustrated in FIG. 3 are disposed so as to be in a symmetric, i.e., a line-symmetric position with respect to each other when the rotary optical transmission system assumes a symmetric position with respect to the stationary optical transmission system.

In that case, both transmission systems will share the refractive index (n1=n2), the inclination angle (θ1=θ2), the refracting angle (θ3 θ4), the focal distance (f1=f2), and the offset amount (δ1=δ2).

Now, for example, in FIG. 3, let the refractive index n1 of the optical fiber FB2 be 1.5, its inclination angle θ1 be 8', and the refractive index n3 of the medium be 1.0 assuming that it is air. Then, the refracting angle θ3 is 12° from the above expression (1). Therefore, when the focal distance f1 of the collimating lens 42 is 2 mm, the above expression (2) gives an offset amount δ1 of 0.14 mm between the central axis of the optical fiber FB2 and the central axis of rotation. Accordingly, where said two transmission systems are disposed symmetrically, the holders 40a and 48a holding the respective optical fibers FB1 and FB2 may be disposed in such a position with respect to the fixed sleeve 38 and the mounting cylinder 46a, respectively, that the central axes of the optical fibers FB1 and FB2 are offset from the central axis of rotation by 0.14 mm.

The inventive optical rotary adapter is basically configured as described above.

Now, description will be made of the components of the optical tomographic imaging system 10 illustrated in FIG. 1 to which the inventive optical rotary adapter 18 is applied.

As illustrated in FIG. 1, the light source unit 12 comprises a semiconductor optical amplifier 60, an optical splitter 62, a collimating lens 64, a diffraction grating element 66, an optical system 67, and a rotary polygon mirror 68 and emits laser beam La that is frequency-swept with a constant period.

The semiconductor optical amplifier (semiconductor gain medium) 60 emits feeble light upon application of drive current and amplifies incoming light. The semiconductor optical amplifier 60 is connected with an optical fiber FB10. More specifically, one end of the optical fiber FB10 is connected to a part of the semiconductor optical amplifier 60 at which light is emitted, whereas the other end of the optical fiber FB10 is connected to a part of the semiconductor optical amplifier 60 at which light enters. The light emitted from the semiconductor optical amplifier 60 is emitted to the optical fiber FB10 and re-enters the semiconductor optical amplifier 60.

Thus, the semiconductor optical amplifier 60 and the optical fiber FB10, forming an optical path loop, provide an optical resonator. Application of activating electric current to the semiconductor optical amplifier 60 causes a laser beam in the form of pulse to be generated.

The optical splitter 62 is provided on the optical path of the optical fiber FB10 and also connected with an optical fiber FB11. The optical splitter 62 directs part of the light guided through the optical fiber FB10 to the optical fiber FB11.

The collimating lens 64 is disposed at the other end of the optical fiber FB11, i.e., the end thereof not connected with the optical fiber FB10, and collimates the light emitted from the optical fiber FB11.

The diffraction grating element 66 is disposed with a given inclination angle on the optical path of the parallel light produced by the collimating lens 64. The diffraction grating element 66 disperses the parallel light emitted from the collimating lens 64.

The optical system 67 is disposed on the optical path of the light dispersed by the diffraction grating element 66. The optical system 67 comprises a plurality of lenses to refract the light dispersed by the diffraction grating element 66 and collimate the refracted light.

The polygon mirror 68 is disposed on the optical path of the parallel light produced by the optical system 67 to reflect the parallel light. The polygon mirror 68 is a rotary unit that turns at a constant speed in the R1 direction indicated in FIG. 1. It has the shape of a regular octagon in a plane perpendicular to the axis of rotation thereof and comprises lateral planes (planes forming the sides of the octagon) irradiated with the parallel light each formed with reflection surfaces for reflecting the light irradiating the planes.

The polygon mirror 68 turns to vary the angle of the reflection surfaces with respect to the optical axis of the optical system 67.

The light emitted from the optical fiber FB11 passes through the collimating lens 64, the diffraction grating element 66, and the optical system 67 and is reflected by the polygon mirror 68. The reflected light passes through the optical system 67, the diffraction grating element 66, and the collimating lens 64 and enters the optical fiber FB11.

Since the angle of the reflection surfaces of the rotary polygon mirror 68 varies with respect to the optical path of the optical system 67 as described above, the angle at which the rotary polygon mirror 68 reflects the light varies with time. Accordingly, only the light having a particular frequency range out of the light dispersed by the diffraction grating element 66 re-enters the optical fiber FB11. Thus, since the light having a particular frequency range entering the optical fiber FB11 is determined by the angle formed by the optical axis of the optical system 67 and the reflection surface of the rotary polygon mirror 68, the frequency range of the light entering the optical fiber FB11 varies with the angle formed by the optical axis of the optical system 67 and the reflection surface of the rotary polygon mirror 68.

The light having a particular frequency range allowed to enter the optical fiber FB11 is delivered through the optical coupler 62 to the optical fiber FB10 and combined with the light of the optical fiber FB10. Thus, the laser beam in the form of pulse guided to the optical fiber FB10 becomes a laser beam having a particular frequency range and this laser beam La having a particular frequency range is emitted to the optical fiber FB3.

Since the polygon mirror 68 is turning at a constant speed in the direction indicated by the arrow R1, the wavelength λ of the light re-entering the optical fiber FB11 varies with a constant period as time passes. Accordingly, the frequency of the laser beam La emitted to the optical fiber F33 also varies with a constant period as time passes.

The light source unit 12 is configured as described above and emits the wavelength-swept laser light La to the optical fiber FB3.

Next, the splitter/combiner 14 is composed, for example, of a 2×2 optical fiber coupler and optically connected with the optical fiber FB2, the optical fiber FB3, the optical fiber FB4, and the optical fiber FB5.

The splitter/combiner 14 splits the incoming light La delivered from the light source unit 12 through the optical fiber FB3 into the measuring light L1 and the reference light L2, directing the measuring light L1 to the optical fiber FB2 and the reference light L2 to the optical fiber FB5.

Further, the splitter/combiner 14 combines the reference light L2, which enters the optical fiber FB5, undergoes frequency shift and optical path length modification effected by an optical path length adjuster 26 to be described, and returns through the optical fiber FB5 to enter the splitter/combiner 14, with the returning light L3 from the object under measurement S, which is acquired by an optical probe to be described and enters the splitter/combiner 14 through the optical fiber FB2. The splitter/combiner 14 emits the combined light to the optical fiber FB4.

The optical probe 16 is connected to the optical fiber FB2 through the optical rotary adapter 18 such that the measuring light L1 is delivered from the optical fiber FB2 to the optical fiber FB1 through the optical rotary adapter 18; the measuring light L1 is then further transmitted by the optical fiber FB1 to irradiate the object under measurement S and acquire the returning light L3 from the object under measurement S; and the returning light L3 thus acquired is transmitted by the optical fiber FB1 to the optical fiber FB2 through the optical rotary adapter 18.

Figure 4:
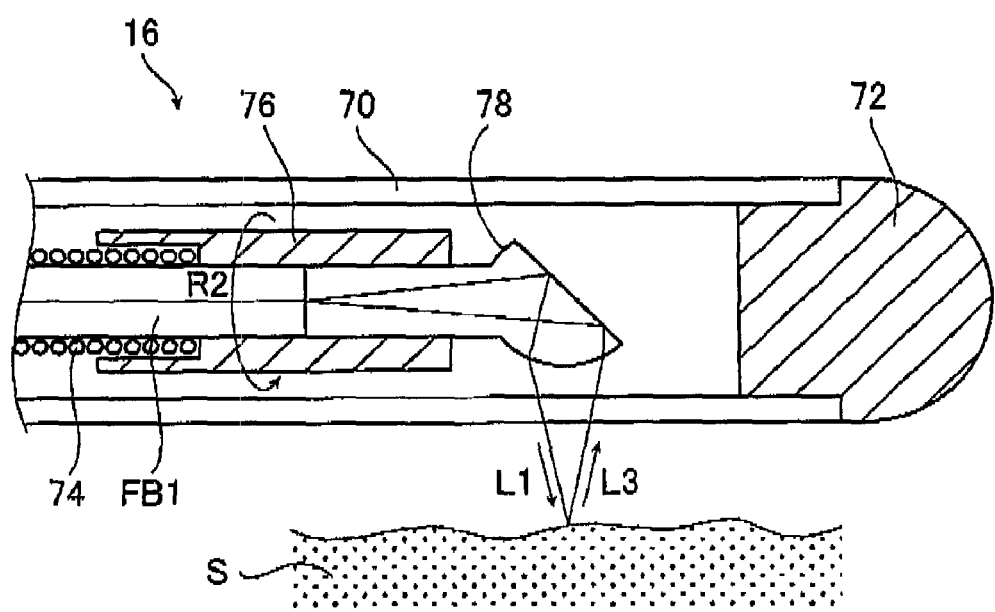
FIG. 4 is a partial, sectional view illustrating an embodiment of an optical probe used for the optical tomographic imaging system of FIG. 1, with the tip of the optical probe shown enlarged.

As illustrated in FIG. 4, the optical probe 16 comprises a probe sheath 70, a cap 72, an optical fiber FB1, a spring 74, a mounting member 76, and an optical lens 78.

The probe sheath 70 is a cylindrical member having a flexibility and formed of a material permitting transmission of the measuring light L1 and the returning light L3. The probe sheath 70 has at least part thereof close to its tip, i.e., an end thereof at which the measuring light L1 and the returning light L3 pass the probe sheath 70 (the end being opposite from the optical fiber FB1, referred to as "the tip of the probe sheath 70" below), formed all the way around circumferentially of a material permitting transmission of light (transparent material).

The cap 72 is provided on the tip of the probe sheath 70 to close the tip of the probe sheath 70.

The optical fiber FB1 is a linear member and encased in the probe sheath 70 along the length thereof; it guides the measuring light L1 delivered from the optical fiber FB2 through the optical rotary adapter 18 to an optical lens 78 and guides the returning light L3 from the object under measurement S acquired by the optical lens 78 by irradiating the object under measurement S with the measuring light L1 to the optical rotary adapter 18, the returning light L3 then entering the optical fiber FB2.

The optical fiber FB1 and the optical fiber FB2 are connected by the optical rotary adapter 18; they are optically connected such that the rotation of the optical fiber FB1 is not conveyed to the optical fiber FB2. The optical fiber FB1 is provided rotatably in relation to the probe sheath 70.

The spring 74 is secured to the periphery of the optical fiber FB1. The optical fiber FB1 and the spring 74 are connected to the optical rotary adapter 18.

The optical lens 78 is disposed at the measuring end of the optical fiber FB1 (the end of the optical fiber FB1 opposite from the optical rotary adapter 18) and has an end formed to have a substantially spherical shape to focus the measuring light L1 delivered from the optical fiber FB1 onto the object under measurement S.

The optical lens 78 irradiates the object under measurement S with the measuring light L1 delivered from the optical fiber FB1 and directs the returning light L3 from the object under measurement S to the optical fiber FB1.

The mounting member 76 is disposed on the periphery over the joint between the optical fiber FB1 and the optical lens 78 to secure the optical lens 78 to the end of the optical fiber FB1. The mounting member 76 may secure the optical fiber FB1 and the optical lens 78 by any of the methods including but not limited to a method using an adhesive material to bond the mounting member 76 to the optical fiber FB1 and the optical lens 78 and a method using a mechanical structure including bolts. The mounting member 76, as with the ferrules 41 and 49 described earlier, may be any appropriate member such as a zirconia ferrule or a metal ferrule used for securing, holding and protection.

As described above, the optical fiber FB1 and the spring 74 are connected to the rotary assembly 46 (the connecting unit 46c of the rotary cylinder 46b) of the optical rotary adapter 18, and rotation of the optical fiber FB1 and the spring 74 by means of the rotary cylinder 46b causes the optical lens 78 to turn in relation to the probe sheath 11 in the direction indicated by the arrow R2 in FIG. 4. The optical rotary adapter 18 has a rotary encoder (not shown) to detect the irradiation position of the measuring light L1 according to the position information (angular information) on the optical lens 78 based on the signal given by the rotary encoder. That is, the measuring position is determined by detecting the angle of the rotating optical lens 78 with respect to a reference position in the direction of rotation.

As the optical rotary adapter 18 turns the optical fiber FB1 and the spring 74 in the direction indicated by the arrow R2 in FIG. 4, the optical probe 16, configured as described above, irradiates the object under measurement S with the measuring light L1 emitted from the optical lens 78 by scanning in the direction indicated by the arrow R2 (in the circumferential direction of the probe sheath 70) and acquires the returning light L3.

Thus acquired is the returning light L3 for the whole circumference of the probe sheath 70 as it is reflected by the object under measurement S.

The optical path length adjuster 26 is disposed on the emission side of the optical fiber FB5 from which the reference light L2 is emitted (i.e., at the end of the optical fiber FB5 opposite from the splitter/combiner 14).

The optical path length adjuster 26 comprises a first optical lens 80 for collimating the light emitted from the optical fiber FB5, a second optical lens 82 for focusing the light collimated by the first optical lens 80, a reflecting mirror 84 for reflecting the light focused by the second optical lens 82, a base 86 for supporting the second optical lens 82 and the reflecting mirror 84, and a mirror moving mechanism 88 for moving the base 86 in the direction parallel to the optical axis. The optical path length adjuster 26 adjusts the optical path length of the reference light L2 by varying the distance between the first optical lens B0 and the second optical lens 82.

The first optical lens 80 collimates the reference light L2 emitted from the core of the optical fiber FB5 and focuses the reference light L2 reflected by the reflecting mirror 84 onto the core of the optical fiber FB5.

The second optical lens 82 focuses the reference light L2 collimated by the first optical lens 80 onto the reflecting mirror 84 and collimates the reference light L2 reflected by the reflecting mirror 84. Thus, the first optical lens 80 and the second optical lens 82 form a confocal optical system.

The reflecting mirror 84 is disposed at the focal point of the light focused by the second optical lens 82 and reflects the reference light L2 focused by the second optical lens 82.

Thus, the reference light L2 emitted from the optical fiber FB5 is collimated by the first optical lens 80 and focused by the second optical lens 82 onto the reflecting mirror 84. Subsequently, the reference light L2 reflected by the reflecting mirror 84 is collimated by the second optical lens 82 and focused by the first optical lens 80 onto the core of the optical fiber FB5.

The base 86 fixedly holds the second optical lens 82 and the reflecting mirror 84 in position while the mirror moving mechanism 88 moves the base 86 in the direction of the optical axis of the first optical lens 80 (the direction indicated by the arrow A in FIG. 1).

The movement of the base 86 effected by the mirror moving mechanism 88 in the direction indicated by the arrow A changes the distance between the first optical lens 80 and the second optical lens 82, permitting the adjustment of the optical path length of the reference light L2.

The interference light detector 20 is connected with the optical fiber FB4 and detects as interference signal the interference light L4 produced by the splitter/combiner 14 by combining the reference light L2 and the returning light L3.

The optical tomographic imaging system 10 comprises the optical fiber coupler 28 for splitting the laser beam La from the optical fiber FB3 and directing the split laser beam La to the optical fiber FB6, the detector 30a provided on the optical path of the optical fiber FB6 split from the optical fiber coupler 28 for detecting the optical intensity of the split laser beam, and the detector 30b disposed on the optical path of the optical fiber FB4 for detecting the optical intensity of the interference light L4.

The interference light detector 20 adjusts the balance of the optical intensity of the interference light L4 detected from the optical fiber FB4 according to the results of the detection performed by the detector 30a and the detector 30b.

From the interference signal detected by the interference light detector 20, the processor 22 detects the area where the optical probe 16 in the measuring position is in contact with the object under measurement S or, more precisely, the area where the surface of the probe sheath 70 may be considered to be in contact with the surface of the object under measurement S, and acquires a tomographic image from the interference signal detected by the interference light detector 20.

Figure 5:
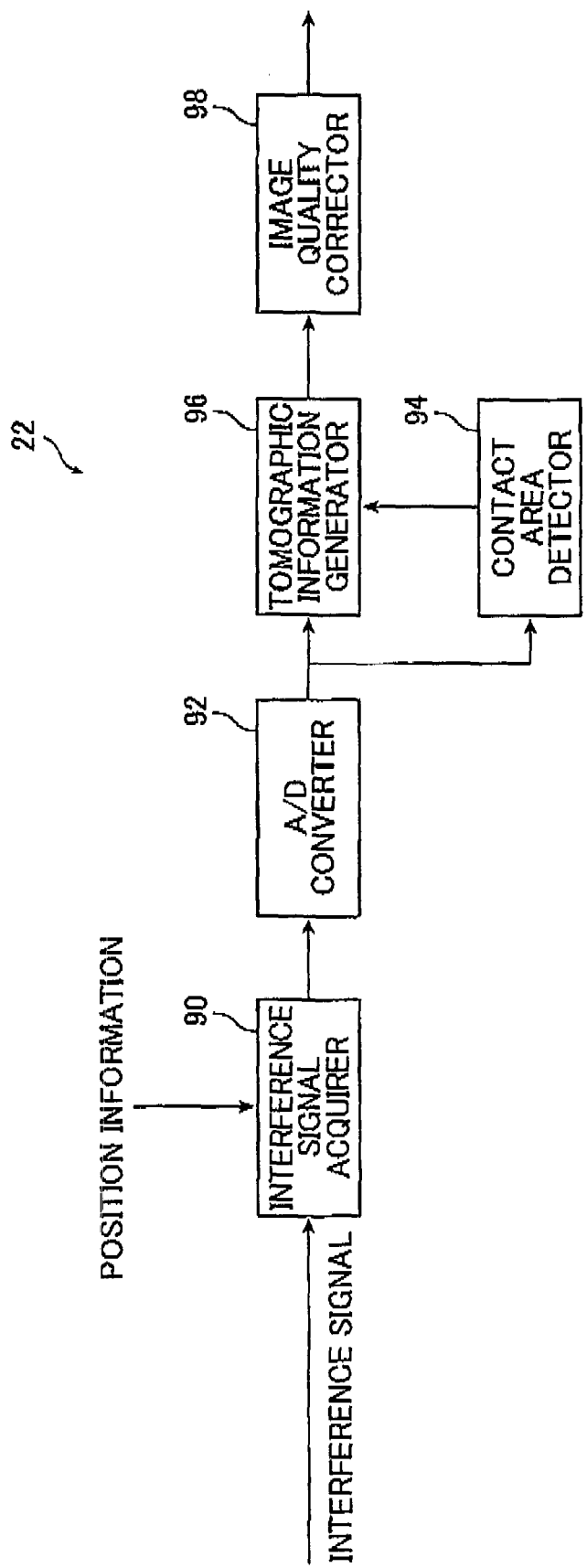
FIG. 5 is a block diagram schematically illustrating a configuration of an embodiment of the processor in the optical tomographic imaging system of FIG. 1.

As illustrated in FIG. 5, the processor 22 comprises an interference signal acquirer 90, an analog-to-digital converter 92, a contact area detector 94, a tomographic information generator 96, and an image quality corrector 98.

The interference signal acquirer 90 acquires the interference signal detected by the interference light detector 20 and acquires information on a measuring position detected by the optical rotary adapter 18, more specifically, position information on the measuring position detected from the information on a position of the optical lens 78 in the rotating direction, and correlates the interference signal with the position information on the measuring position.

The interference signal correlated with the position information on the measuring position is sent to the analog-to-digital converter 92.

The analog-to-digital converter 92 converts to digital signal the interference signal produced from the interference signal acquirer 90 as analog signal correlated with the position information on the measuring position.

The interference signal now correlated with the position information on the measuring position and converted to digital signal is sent to the contact area detector 94 and the tomographic information generator 96.

The contact area detector 94 applies fast Fourier transform (FFT) to the interference signal now converted to digital signal by the analog-to-digital converter 92 to acquire the relationship between frequency component and intensity of the interference signal and associates the frequency component, which is now correlated with the intensity, with the depth direction (the direction in which the distance from the center of rotation increases) to acquire information on the relationship between depth direction and intensity. From the information on the relationship between depth direction and intensity the contact area detector 94 detects the position on the surface of the probe sheath 70 at which the measuring light L1 is transmitted and the contact area between that position on the surface of the probe sheath 70 at which the measuring light L1 is transmitted and the object under measurement S.

Thus, information on the contact area between the probe sheath 70 and the object under measurement S is sent to the tomographic information generator 96.

The tomographic information generator 96 processes the information on the relationship between frequency component and intensity obtained by fast Fourier transform applied to the interference signal converted to digital signal by the analog-to-digital converter 92 to acquire a depthwise tomographic image.

The tomographic information generator 96 only acquires a tomographic image from the interference signal of the information on a position judged to be the contact area from among the contact area information sent from the contact area detector 94 and acquires no tomographic image from an interference signal of the information on a position representing an area other than the contact area, that is, performs no FFT or no image acquisition processing from the results obtained by application of FFT, performing instead a masking process.

Now, description will be briefly made on the generation of an image performed by the tomographic information generator 96. Let S(1) be the optical intensity of interference fringes for each optical path length difference 1 of the various optical path length differences with which the returning light L3 from the respective depths in the object under measurement S interferes with the reference light L2 as the measuring light L1 irradiates the object under measurement S. Then, the optical intensity I(k) of the interference signal detected in the interference light detector 20 is expressed by an expression:

$$I(k)=\int_0^\infty S(1)[1+\cos(k1)]dl$$

where k is the number of waves and l the optical path length difference. The above expression may be considered to represent an interferogram for a frequency range having the number of waves k=ω/c as a variable. Accordingly, applying fast Fourier transfer to the spectral interference fringes detected by the interference light detector 20 and determining the optical intensity S(1) of the interference light L4 in the tomographic information generator 96 yield information on the distance from the measurement starting position of the object under measurement S and reflection intensity information, thereby generating a tomographic image.

The image quality corrector 98 performs logarithmic conversion and radial conversion of the tomographic image generated by the tomographic information generator 96 to obtain a circular image centering about the center of rotation of the optical lens 78.

The image quality corrector 98 further performs sharpening processing, smoothing processing and the like on the tomographic image to correct the image quality.

The image quality corrector 98 sends the tomographic image with image quality corrected to the display 24.

The tomographic image may be sent at any appropriate timing; it may be sent to the display each time processing for one scan line is completed to effect rewrite each time one scan line is provided, or may be sent when processing for all the scan lines is completed (that is, when processing is completed to acquire an image as the optical lens has completed its one full rotation) to generate a circular tomographic image.

The display 24, which may be a CRT, a liquid crystal display device or the like, displays the tomographic image sent from the image quality corrector 98.

The operation control 32 comprises entry means such as a keyboard and a mouse, and control means for controlling various conditions according to the entered information and is connected to the processor 22 and the display 24. The operation control 32 performs, among others, entry, setting and change of thresholds, various processing conditions, etc. in the processor 22 and change of display settings in the display 24 according to the operator instructions entered at the entry means. The operation screen for the operation control 32 may be given on the display 24 or may be displayed on a separately provided monitor. The operation control 32 may be adapted to perform operation controls and settings of various conditions for the light source unit 12, the optical rotary adapter 18, the interference light detector 20, the optical path length adjuster 26 and the detectors 30a and 30b.

The optical tomographic imaging system 10 of the invention is basically configured as described above.

Next, the operations of the inventive optical tomographic imaging system 10 and the inventive optical rotary adapter 18 will be described.

Description will be first made as to how the interference light and then the interference signal are acquired upon measuring the object under measurement S.

First, the mirror moving mechanism 88 is activated to move the base 86 in the direction indicated by the arrow A to adjust and set the optical path length such that the object under measurement S is positioned within a measurable range.

Subsequently, the light source unit 12 emits the laser beam La. The emitted laser beam La is split by the splitter/combiner 14 into the measuring light L1 and the reference light L2. The measuring light L1 is guided through the optical fiber FB2, the inventive optical rotary adapter 18, and the optical probe 16 (optical fiber FB1) to radiate the object under measurement S.

The inventive optical rotary adapter 18 meanwhile is rotating the optical fiber FB1 and the optical lens 78 in the optical probe 16. More specifically, in the optical rotary adapter 18 of the invention, the motor 36 is activated to turn the rotary shaft 36a and the gear 54 mounted at the end thereof, causing the gear 52 in mesh with the gear 54 to turn. By the intermediate of the rotary cylinder 46b of the rotary assembly 46, the rotation of the gear 52 turns the mounting cylinder 46a rotatably carried by the fixed sleeve 38 via the bearings 44. This in turn rotates the optical fiber FB1 held substantially at the center of the mounting cylinder 46a by the holder 48a, etc. Since the optical fiber FB1 held inside the rotary assembly 46 (rotary cylinder 46b) is connected to the optical fiber FB1 encased in the optical probe 16 at the connecting unit 46c of the rotary cylinder 46b or extends into the optical probe 16 via the connecting unit 46c of the rotary cylinder 46b of the rotary cylinder 46b, the rotation of the optical fiber FB1 encased in the rotary cylinder 46b turns the optical fiber FB1 inside the optical probe 16 and the optical lens 78 that is attached at the tip thereof.

Meanwhile, the measuring light L1 transmitted by the optical fiber FB2 held by the holder 40a of the fixed sleeve 38 and emitted from the inclined end face of the optical fiber FB2 enters the collimating lens 42 held by the holder 40b of the fixed sleeve 38 and then, after collimation, the collimating lens 50 held by the holder 48b attached to the rotating mounting cylinder 46a. The measuring light L1 is then focused and allowed to enter the inclined end face of the optical fiber FB1 held by the holder 48a mounted to the holder 48b. The measuring light L1 is then transmitted into the optical fiber FB1 inside the optical probe 16 to enter the optical lens 78 and directed by the optical lens 78 to pass through the probe sheath 70, irradiating the object under measurement S.

Since the optical rotary adapter 18 is meanwhile rotating the optical fiber FB1 and the optical lens 78 in the optical probe 16, the object under measurement S such as a bodily cavity is irradiated with the measuring light L1 throughout the circumference thereof by means of the rotating optical lens 78. Meanwhile, the optical rotary adapter 18 detects information on the measuring position of the object under measurement S using a rotary encoder (not shown).

Subsequently, the light reflected at individual depth positions of the object under measurement S enters the optical probe 16 as the returning light L3. Since the optical rotary adapter 18 is still rotating the optical fiber FB1 and the optical lens 78 inside the optical probe 16, the returning light L3 from the object under measurement S for the whole circumference of the object under measurement S enters the rotating optical lens 78. This returning light L3 is delivered to the splitter/combiner 14 through the optical probe 16 (optical fiber FB1), the optical rotary adapter 18, and the optical fiber FB2.

The returning light L3 from the object under measurement S is transmitted through the probe sheath 70 of the optical probe 16 to enter the rotating optical lens 78, then transmitted therefrom to the optical fiber FB1 in the optical probe 16, and enters the optical fiber FB1 held by the holder 48a inside the rotary assembly 46 of the optical rotary adapter 18. In the optical rotary adapter 18, the returning light L3 emitted from the inclined end face of the rotating optical fiber FB1 enters the collimating lens 50 held by the holder 48b inside the rotating rotary assembly 46 and, after collimation, the collimating lens 42 held by the holder 40b of the stationary fixed sleeve 38. The returning light L3 is then focused to enter the inclined end face of the optical fiber FB2 held by the holder 40a of the fixed sleeve 38 and delivered through the optical fiber FB2 to the splitter/combiner 14.

In the optical rotary adapter 18, since the central axes of the rotary optical fiber FB1 and the stationary optical fiber FB2 are offset from the center of rotation, i.e. the center of rotation of the rotary assembly 46 (mounting cylinder 46a), each by a given amount, the attenuation of the returning light L3 can be lessened to reduce white noise and improve the signal-to-noise ratio of the returning light L3.

Meanwhile, the reference light L2 is delivered through the optical fiber FB5 to the optical path length adjuster 26. The reference light L2 having its optical path length adjusted by the optical path length adjuster 26 is guided through the optical fiber FB5 back to the splitter/combiner 14.

The splitter/combiner 14 combines the returning light L3 from the object under measurement S with the reference light L2 having its optical path length adjusted by the optical path length adjuster 26, generating the interference light L4 from the returning light L3 and the reference light L2. The interference light is detected as interference signal by the interference light detector 20.

Then, the interference signal detected by the interference light detector 20 is sent to the processor 22.

In the processor 22, the interference signal acquirer 90 acquires the interference signal it receives as well as information on the measuring position detected by the optical rotary adapter 18 to correlate the interference signal with the information on the measuring position.

Then, the analog-to-digital converter 92 converts the interference signal acquired by the interference signal acquirer 90 and correlated with the information on the measuring position from analog signal to digital signal. The interference signal now correlated with the information on the measuring position and converted to digital signal is sent from the analog-to-digital converter 92 to the contact area detector 94 and the tomographic information generator 96.

The contact area detector 94 detects the contact area of the probe sheath 70 and the object under measurement S, whereon the information on the detected contact area of the probe sheath 70 and the object under measurement S is sent to the tomographic information generator 96.

From the contact area information sent from the contact area detector 94, the tomographic information generator 96 processes the information on the relationship between frequency component and intensity obtained by applying FFT to the interference signal converted into digital signal by the analog-to-digital converter 92 only where the interference signal is correlated with the information on the position judged to be a contact area to acquire a depthwise tomographic information for the contact area. The tomographic image acquired by the tomographic information generator 96 is sent to the image quality corrector 98.

The image quality corrector 98 performs logarithmic conversion and radial conversion on the tomographic image generated by the tomographic information generator 96 to make it a circular tomographic image the center of which registers with the center of rotation of the optical lens 78, as well as sharpening processing and smoothing processing and the like to correct the image quality.

The tomographic image with the image quality corrected by the image quality corrector 98 is sent to the display 24.

The display 24 shows the tomographic image sent from the image quality corrector 98 as an image after image quality correction.

While the optical rotary adapter 18 illustrated in FIGS. 2 and 3 has the rotary optical fiber FB1 and the stationary optical fiber FB2 disposed with their central axes offset each by a given amount from the central axis of rotation of the mounting cylinder 46a of the rotary assembly 46, the invention is not limited to such a configuration; the central axes of the rotary optical fiber FB1 and the stationary optical fiber FB2 may be inclined each a given angle with respect to the central axis of rotation of the mounting cylinder 46a of the rotary assembly 46.

Figure 6:
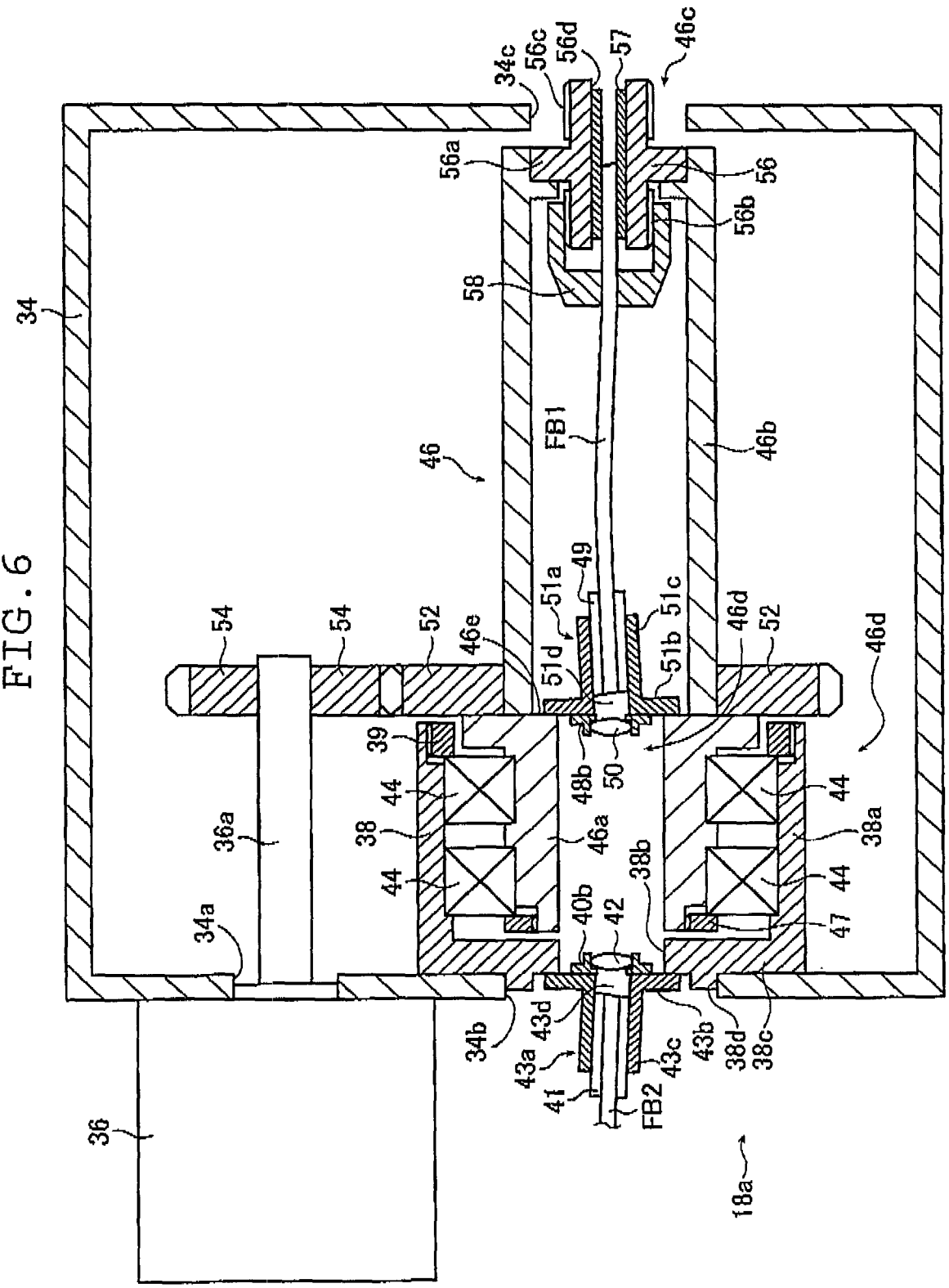
FIG. 6 is a schematic sectional view illustrating a configuration of another embodiment of the optical rotary adapter illustrated in FIG. 1.
Figure 7:
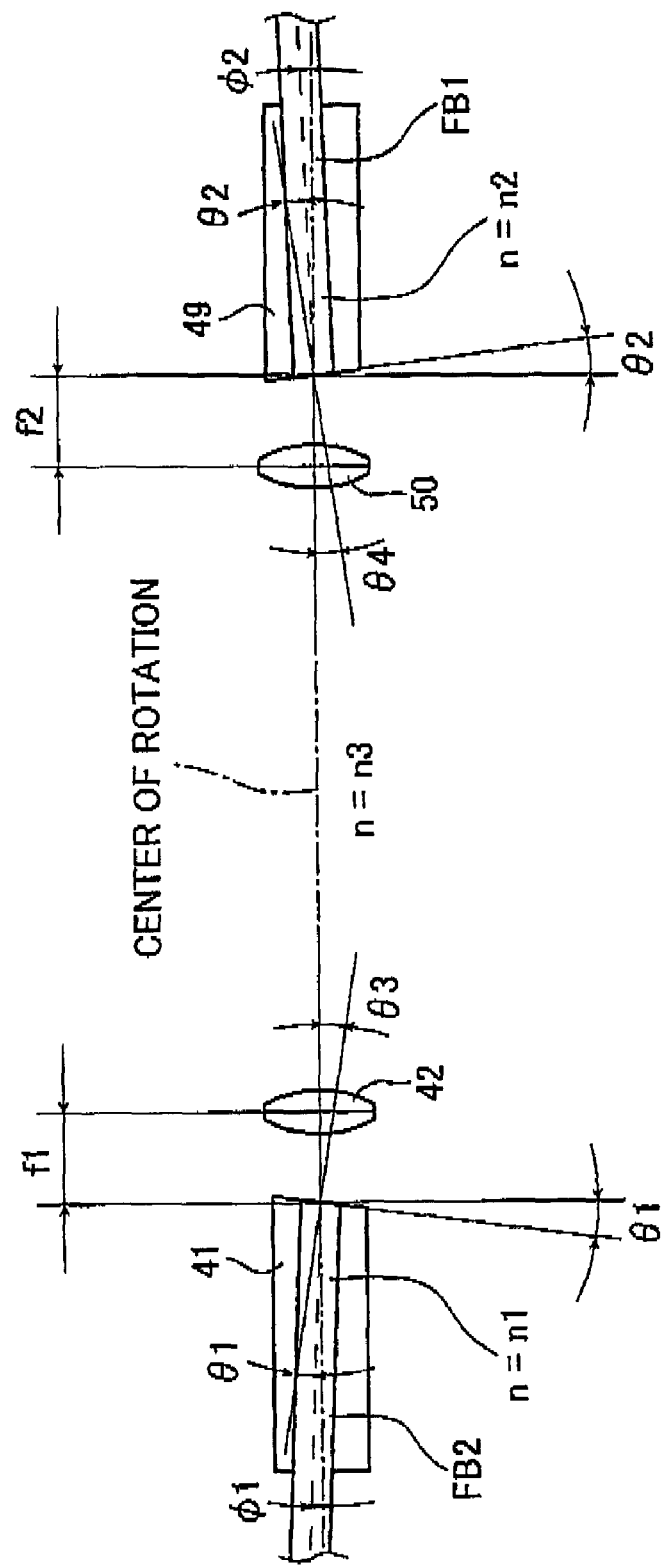
FIG. 7 is a view for explaining an example of the positional relationship of the optical fibers and the collimating lenses with respect to the center of rotation of the optical rotary adapter illustrated in FIG. 6.

FIG. 6 is a schematic sectional view of another embodiment of such an optical rotary adapter of the invention; FIG. 7 is a view for explaining an example of the positional relationship of optical fibers and collimating lenses with respect to the center of rotation of the optical rotary adapter illustrated in FIG. 6.

An optical rotary adapter 18a illustrated in FIG. 6 is used for the optical tomographic imaging system 10 illustrated in FIG. 1 in place of the optical rotary adapter 18 illustrated in FIG. 2. The optical rotary adapter 18a has a configuration similar to that of the optical rotary adapter 18 illustrated in FIG. 2 except that while the stationary optical fiber F52 and the ferrule 41 are secured with the holder 40a to the fixed sleeve 38 and the rotary optical fiber FB1 and the ferrule 49 are secured with the holder 48a to the mounting cylinder 46a of the rotary assembly 46 so as to be offset from the central axis of rotation of the mounting cylinder 46a each by a given amount (say δ1 (see FIG. 3)) in the optical rotary adapter 18, the stationary optical fiber FB2 and the ferrule 41 are secured with a holder 43a to the fixed sleeve 38 and the rotary optical fiber FB1 and the ferrule 49 are secured with a holder 51a to the mounting cylinder 46a of the rotary assembly 46 so as to be inclined each a given angle (say φ1 (see FIG. 7)) with respect to the central axis of rotation of the mounting cylinder 46a in the optical rotary adapter 18a. Thus, like reference numerals indicate like components and detailed description thereof will not be repeated.

The optical rotary adapter 18a illustrated in FIG. 6 comprises the casing 34, the motor 36, the fixed sleeve 38, the stationary optical fiber FB2 and the stationary collimating lens 42 secured respectively with the holders 43a and 40b that in turn are fixedly attached to the center of one end face of the fixed sleeve 38, the rotary assembly 46 essentially composed of the mounting cylinder 46a and the rotary cylinder 46b, the rotary optical fiber FB1 and the rotary collimating lens 50 secured respectively with the holders 51a and 48b that in turn are fixedly mounted to the center of one end face of the mounting cylinder 46a, the gear 52, and the gear 54.

The holder 43a is a flanged circular tubing member for holding the cylindrical ferrule 41 holding the optical fiber FB2 at the center thereof and comprises a flange section 43b having an external end face inclined a given angle (say φ1 (see FIG. 7)) with respect to the central axis of rotation of the mounting cylinder 46a and a straight tubing section 43c having a through-hole 43d holding the cylindrical ferrule 41 at the center thereof.

The holder 43a is only different from the holder 40a illustrated in FIG. 2 in that the external end face of the flange section 43b of the holder 43a is inclined a given angle (say φ1 (see FIG. 7)) or, more specifically, the external end face of the flange section 43b is inclined with respect to the plane perpendicular to the central axis of the straight tubing section 43c while the external end face of the flange section of the holder 40a illustrated in FIG. 2 is perpendicular to, that is, not inclined with respect to, the central axis of the straight tubing section.

As with the holder 40a illustrated in FIG. 2, the holder 43a holds the optical fiber FB2 and the ferrule 41 such that their inclined forward end faces (the inclination angle thereof is θ1, for example (see FIG. 7)) are located a given distance inwardly from the end face of the flange section 43b into the through-hole 43d of the straight tubing section 43c.

The holder 43a is mounted, outwardly directed, such that the inclined external end face of the flange section 43b thereof is secured in close contact with the periphery of the central aperture 38b on the outside of the discal section 38c of the fixed sleeve 38. The periphery of the central aperture 38b on the outside of the discal section 38c of the fixed sleeve 38 forms a plane perpendicular to the central axis thereof (coinciding with the central axis of rotation of the mounting cylinder 46a of the rotary assembly 46). Accordingly, the central axis of the holder 43a or the central axis of the optical fiber FB2 in the holder 43a is inclined a given angle (say φ1 (see FIG. 7)) with respect to the central axis of rotation of the mounting cylinder 46a, and the inclined external end face of the flange section 43b of the holder 43a forms a plane perpendicular to the central axis of rotation of the mounting cylinder 46a.

The flange section 43b of the holder 43a is attached to the periphery of the central aperture 38b on the outside of the discal section 38c such that the center of the inclined end face of the optical fiber FB2 held by the holder 43a by the intermediate of the ferrule 41 lies on the central axis of rotation of the mounting cylinder 46a of the rotary assembly 46 or coincides with the axis of rotation.

The holder 40b is a flanged circular tubing member for holding the collimating lens 42 and is secured, outwardly directed, such that its flange section is in close contact with the periphery of the through-hole 43d located about the center of the external end face of the flange section 43b of the holder 43a and that the center of the end face of the optical fiber FB2 and the center of the collimating lens 42 are spaced from each other on the optical axis thereof by a given distance, specifically the focal distance of the collimating lens 42.

Since the inclined external end face of the flange section 43b of the holder 43a is in close contact with the end face forming the periphery of the central aperture 38b on the outside of the discal section 38c of the fixed sleeve 38, the holder 40b is secured to the holder 43a such that the central axis of the holder 40b or the central optical axis of the collimating lens 42 coinciding therewith coincides with the central axis of rotation of the mounting cylinder 46a. Accordingly, the center of the inclined end face of the optical fiber FB2 and the central optical axis of the collimating lens 42 coincide with the central axis of rotation of the mounting cylinder 46a.

This is how the holders 43a and 40b are fixedly mounted to the fixed sleeve 38.

The flange section of the holder 51a is attached close to the center of the flange section 46e on the rear end of the mounting cylinder 46a of the rotary assembly 46 in such a manner as to cover the central aperture 46d.

The holder 51a is a flanged cylindrical member for holding the cylindrical ferrule 49 holding the optical fiber FB1 at the center thereof and has a flange section 51b with an external end face inclined a given angle (say φ2 (see FIG. 7)) and a straight tubing section 51c having a through-hole 51d holding the cylindrical ferrule 49 at the center thereof.

The holder 51a is only different from the holder 48a illustrated in FIG. 2 in that the external end face of the flange section 51b is inclined a given angle (say φ1 (see FIG. 7)) or, more specifically, the external end face of the flange section 51b is inclined with respect to the plane perpendicular to, that is, not inclined with respect to, the central axis of the straight tubing section 51c while the external end face of the flange section of the holder 48a illustrated in FIG. 2 is perpendicular to the central axis of the straight tubing section.

As with the holder 48a illustrated in FIG. 2, the holder 51a holds the optical fiber FB1 and the ferrule 49 such that their inclined forward end faces (the inclination angle thereof is θ2, for example (see FIG. 7)) are located a given distance inwardly from the end face of the flange section 51b into the through-hole 51d of the straight tubing section 51c.

The holder 51a is secured, outwardly directed, to the mounting cylinder 46a such that the inclined external end face of the flange section 51b thereof is in close contact with the periphery of the central aperture 46d of the flanged end face 46e of the mounting cylinder 46a of the rotary assembly 46. The periphery of the central aperture 46d of the flanged end face 46e of the mounting cylinder 46a forms a plane perpendicular to the central axis thereof (coinciding with the central axis of rotation of the mounting cylinder 46a). Accordingly, the central axis of the holder 51a or at least the central axis of the optical fiber FB1 in the holder 51a is inclined a given angle (say φ2 (see FIG. 7)) with respect to the central axis of rotation of the mounting cylinder 46a, and the inclined external end face of the flange section 51b of the holder 51a forms a plane perpendicular to the central axis of rotation of the mounting cylinder 46a.

The flange section 51b of the holder 51a is attached to the periphery of the central aperture 46d of the flanged end face 46e of the mounting cylinder 46a such that the center of the inclined forward end face of the optical fiber FB1 held by the holder 51a by the intermediate of the ferrule 49 lies on the central axis of rotation of the mounting cylinder 46a.

The holder 48b is, as with the holder 40b, a flanged circular tubing member for holding the collimating lens 50 and is secured, outwardly directed, such that its flange section is in close contact with the periphery of the through-hole 51d located about the center of the external end face of the flange section 51b of the holder 51a and that the center of the forward end face of the optical fiber FB1 and the center of the collimating lens 50 are spaced from each other on the optical axis thereof by a given distance, specifically the focal distance of the collimating lens 5

Since the inclined external end face of the flange section 51b of the holder 51a is in close contact with the end face forming the periphery of the central aperture 46d of the flanged end face 46e of the mounting cylinder 46a, the holder 48b is secured to the holder 51a such that the central axis of the holder 48b or the central optical axis of the collimating lens 50 coinciding therewith coincides with the central axis of rotation of the mounting cylinder 46a. Accordingly, the center of the inclined forward end face of the optical fiber FB1 and the central optical axis of the collimating lens 50 coincide with the central axis of rotation of the mounting cylinder 46a.

In the example illustrated in FIG. 6r the optical fiber FB1 is attached to the mounting cylinder 46a by the intermediate of the holder 51a such that its inclined forward end face is held by the holder 51a with the center thereof lying on the central axis of rotation of the mounting cylinder 46a at the forward end thereof, i.e., in the vicinity of the collimating lens 50, hence coincides with the central axis of rotation, and that the central axis of the optical fiber FB1 is inclined a given angle (φ2 in the example illustrated in FIG. 7) with respect to the central axis of rotation of the mounting cylinder 46a. At the connecting unit 46c on the rear end of the rotary cylinder 46b, the optical fiber FB1 is preferably supported at the center of the rotary cylinder 46b with the end face member 56 and the cap nut 58 such that the central axis of the optical fiber FB1 coincides with the central axis of rotation of the rotary cylinder 46b.

The optical rotary adapter 18a illustrated in FIG. 6 also permits removal of the rotary assembly 46, with the holder 51a holding the optical fiber FB1 attached, by withdrawing the rotary assembly 46 from the fixed sleeve 38 with the holder 43a holding the optical fiber FB2 attached by, for example, removing the rotary cylinder 46b of the rotary assembly 46 and the gear 52 to remove the ring 39, although this may not be readily achieved because of the press-fitted bearings 44.

While the connecting unit 46c of the rotary cylinder 46b of the rotary assembly 46 functions as a connector for the optical fiber according to the configuration of the illustrated example, an alternative configuration may be used where the optical fiber FB1 is held in position by the holder 51a attached to the mounting cylinder 46a, allowing the optical fiber FB1 thus held to extend up to the forward end of the optical probe 16, as with the optical rotary adapter 18.

In the illustrated example of the optical rotary adapter 18a, the central axes of the optical fibers FB1 and FB2 are respectively inclined in the vicinity of the stationary collimating lens 42 and the rotary collimating lens 50 with respect to the lines connecting the centers of the inclined end faces of the optical fibers FB1 and FB2 and the optical axis of the collimating lenses 42 and 50, that is, the central axis of rotation of the rotary assembly 46 (mounting cylinder 46a) to reduce the attenuation of the returning light L3 from the object under measurement and improve the signal-to-noise ratio of the returning light L3.

FIG. 7 is a schematic view illustrating the positional relationship between the stationary optical transmission system composed of the stationary optical fiber FB2 and the stationary collimating lens 42 and the rotary optical transmission system composed of the rotary optical fiber FB1 and the rotary collimating lens 50 as described above.

Now, as illustrated in FIG. 7, let θ1 be the inclination angle between the inclined end face of the stationary optical fiber FB2 with respect to a plane perpendicular to the central axis of the stationary optical fiber FB2, n1 the refractive index of the optical fiber FB2, n3 the refractive index of the medium between the optical fibers FB2 and FB1 that propagates the light excluding the collimating lenses 42 and 50, and θ3 the angle (retracting angle) of the light traveling inside the optical fiber FB2 in the direction parallel to the central axis thereof and refracted at the interface between the inclined end face of the optical fiber FB2 and the medium with respect to the normal line to the inclined end face. Then, the stationary optical fiber FB2 and the collimating lens 42 are preferably secured to the mounting cylinder 46a such that the inclination angle φ1 of the central axis of the optical fiber FB2 with respect to the central axis of rotation of the rotary assembly 46 (mounting cylinder 46a) satisfies the following expressions (5) and (6).

$$n1 \times \sin\theta1 = n3 \times \sin\theta3 \tag{5}$$

$$\phi1 = \theta3 - \theta1 \tag{6}$$

Likewise, as illustrated in FIG. 7, let θ2 be the inclination angle of the inclined forward end face of the rotary optical fiber FB1 with respect to a plane perpendicular to the central axis of the rotary optical fiber FB1, n2 the refractive index of the optical fiber FB1, n3 the refractive index of the above medium propagating the light, and θ4 the angle (refracting angle) of the light traveling inside the optical fiber FB1 in the direction parallel to the central axis thereof and refracted at the interface between the inclined end face and the medium and the normal line to the inclined end face. Then, the rotary optical fiber FB1 and the collimating lens 50 are preferably mounted to the mounting cylinder 46a such that the inclination angle φ2 of the central axis of the optical fiber FB1 with respect to the central axis of rotation of the mounting cylinder 46a satisfies the following expressions (7) and (8).

$$n2 \times \sin\theta2 = n3 \times \sin\theta4 \tag{7}$$

$$\phi2 = \theta4 - \theta2 \tag{8}$$

In FIG. 7, where reference characters f1 and f2 denote the focal distances of the collimating lenses 42 and 50, respectively, it is preferable that the distance along the optical axis between the center of the inclined end face of the optical fiber FB2 and the center of the collimating lens 42 is equal to the focal distance f1 of the collimating lens 42 on the assumption that the collimating lens 42 is a thin sheet lens and that the distance along the optical axis between the center of the inclined end face of the optical fiber FB1 and the center of the collimating lens 50 is equal to the focal distance f2 of the collimating lens 50 on the assumption that the collimating lens 50 is a thin sheet lens.

As described above, the provision of the stationary optical transmission system composed of the stationary optical fiber FB2 and the stationary collimating lens 42 and the rotary optical transmission system composed of the rotary optical fiber FB1 and the rotary collimating lens 50 illustrated in FIG. 7 also achieves lessening the attenuation of the returning light L3 from the object under measurement to reduce white noise and improve the signal-to-noise ratio of the returning light L3.

The stationary optical transmission system composed of the stationary optical fiber FB2 and the stationary collimating lens 42 and the rotary optical transmission system composed of the rotary optical fiber FB1 and the rotary collimating lens 50 illustrated in FIG. 7 may be disposed in any positional relationship, provided that the above expressions (5) to (8) are satisfied and preferably disposed in a symmetric, i.e., a line-symmetric position with respect to each other when the rotary optical transmission system assumes a symmetric position with respect to the stationary optical transmission system.

In that case, both transmission systems will share the refractive index (n1=n2), the inclination angle (θ1=θ2), the refracting angle (θ3=θ4), the focal distance (f1=f2), and the inclination angle (φ1=φ2).

Now, for example, in FIG. 7, let the refractive index n1 of the optical fiber FB2 be 1.5, its inclination angle θ1 be 8°, and the refractive index n3 of the medium be 1.0 assuming that it is air. Then, the refracting angle θ3 is 12° from the above expression (1). Therefore, the inclination angle of the central axis of the optical fiber FB2 with respect to the central axis of rotation of the rotary cylinder is 4° from the above expression (6). Accordingly, where said two transmission systems are disposed symmetrically, the holders 43a and 51a holding the respective optical fibers FB1 and FB2 may be disposed with respect to the fixed sleeve 38 and the mounting cylinder 46a, respectively, such that the central axes of the optical fibers FB1 and FB2 are inclined by 4° with respect to the central axis of rotation.

As described above, accidental damage or break of the connecting ends of the optical fibers FB1 and FB2 may be prevented also according to the configuration of the optical rotary adapter 18a illustrated in FIGS. 6 and 7 as with the optical rotary adapter 18 illustrated in FIGS. 2 and 3. In addition, the attenuation of the returning light from the object under measurement and decrease in the signal-to-noise ratio due to the reflection at the opposite end faces of both optical fibers FB1 and FB2 connected can also be prevented.

In the example illustrated in FIG. 6, the external end faces of the flanges 43b and 51b of the respective holders 43a and 51a holding the optical fibers FB1 and FB2 respectively are inclined end faces inclined each a given angle with respect to a plane perpendicular to the central axes of the respective straight tubing sections 43c and 51c, and these inclined end faces are secured in close contact to the periphery of the central aperture 38b on the outside of the discal section 38c of the fixed sleeve 38 and the periphery of the central aperture 46d of the flanged end face 46e of the mounting cylinder 46a of the rotary assembly 46, respectively, such that the central axes of the optical fiber FB1 and the optical fiber FB2 are inclined each a given angle with respect to the central axis of rotation of the mounting cylinder 46a. The invention, however, is not limited to such a configuration, provided that the central axes of the optical fiber FB1 and the optical fiber FB2 are inclined each a given angle with respect to the central axis of rotation of the mounting cylinder 46a. For example, instead of inclining the external end faces of the flanges of the holders holding the optical fibers FB1 and FB2, the through-holes of the tubing sections of the respective holders may be adapted to be inclined each a given angle to hold therein the ferrules 41 and 49 holding the optical fibers FB1 and FB2, respectively, at the cores thereof such that the central axes of the optical fibers FB1 and FB2 are inclined each a given angle with respect to the central axis of rotation of the mounting cylinder 46a.

In the optical tomographic imaging system 10 described above and illustrated in FIG. 1, the splitter/combiner 14 is provided as a single unit to split the light La emitted by the light source unit 12 into the measuring light L1 and the reference light L2 and combine the returning light L3 from the object under measurement, a sample under test, and the reference light L2 to produce the interference light L4. The invention is not limited to such a configuration; a splitter and a combiner may be provided separately such that the splitter splits the emitted light La into the measuring light L1 and the reference light L2 while the combiner combines the returning light L3 from the object under measurement and the reference light L2 to produce the interference light L4.

Figure 8:
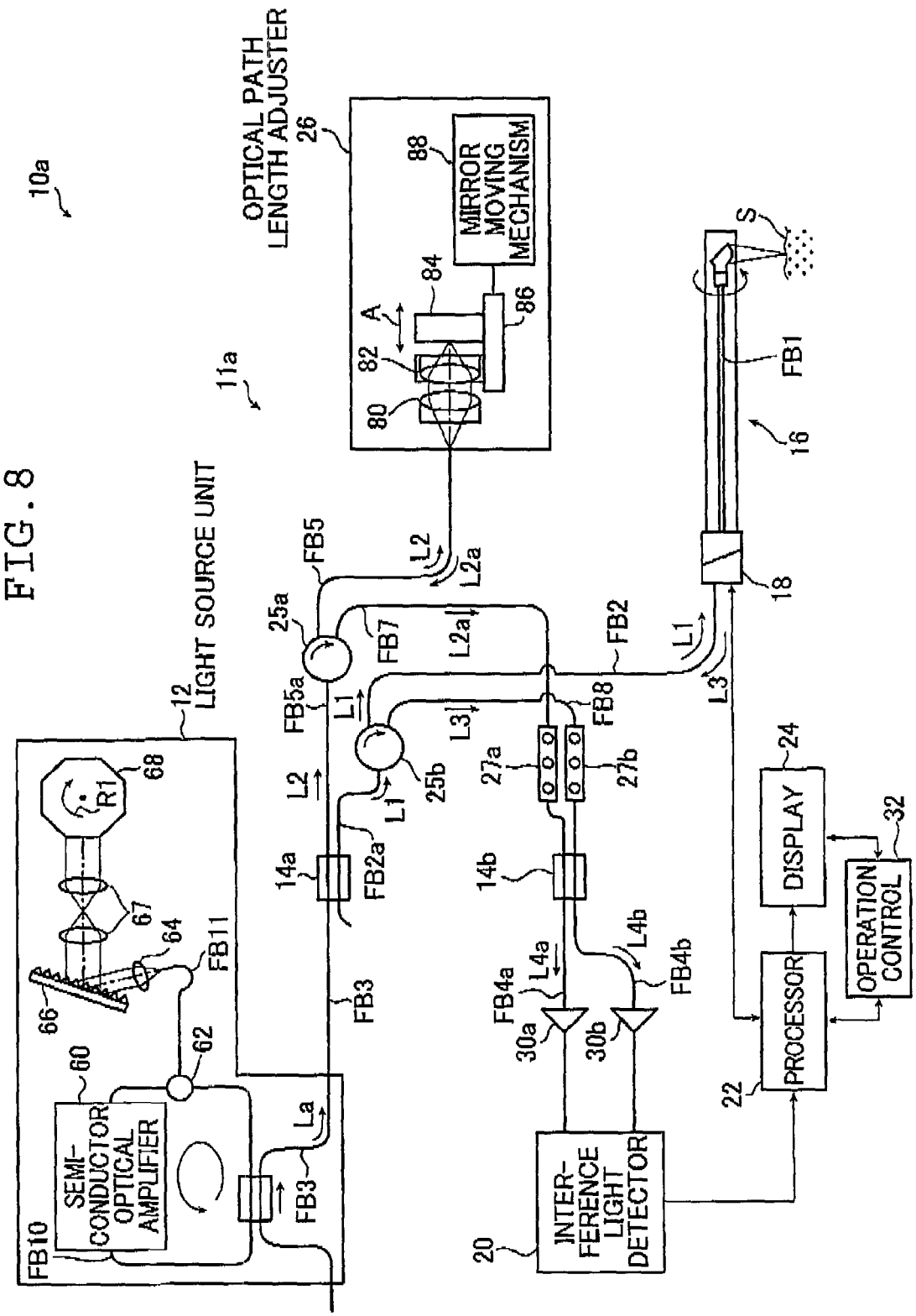
FIG. 8 is a block diagram schematically illustrating a configuration of another embodiment of the inventive optical tomographic imaging system using the inventive optical rotary adapter.

FIG. 8 is a schematic sectional view of another embodiment of such an optical tomographic imaging system of the invention. While, as with the optical tomographic imaging system 10 illustrated in FIG. 1, an optical tomographic imaging system 10a illustrated in FIG. 8 may use either of the optical rotary adapter 18 illustrated in FIGS. 2 and 3 and the optical rotary adapter 18a illustrated in FIGS. 5 and 6, description will be made of the optical tomographic imaging system 10a using the optical rotary adapter 18 illustrated in FIGS. 2 and 3 as a representative example.

The optical tomographic imaging system 10a illustrated in FIG. 8 has a similar configuration to that of the optical tomographic imaging system 10 illustrated in FIG. 1 except that the former comprises a splitter 14a, a combiner 14b, optical circulators 25a and 25b and polarization controllers 27a and 27b in place of the splitter/combiner 14 and the optical fiber coupler 28 in a main body of the system 11a. Thus, like reference characters indicate like components, of which detailed description will not be repeated.

The optical tomographic imaging system 10a illustrated in FIG. 8 comprises:

a main body of the system 11a including the light source unit 12, the splitter 14a for splitting the light La emitted by the light source unit 12 into the measuring light L1 and the reference light L2, the combiner 14b for combining the returning light L3 from the object under measurement or the sample under test and the reference light L2 to produce interference light L4a and L4b, the interference light detector 20 for detecting interference signal based on the interference light L4a and L4b produced by the combiner 14b, the processor 22 for processing the interference signal to acquire an optical tomographic image, and the display 24 for displaying the tomographic image;

the optical probe 16 having the rotary optical fiber FB1 for guiding the measuring light L1 split by the splitter 14a of the main body of the system 11a to the object under measurement and for guiding the returning light L3 from the object under measurement;

the stationary optical fiber FB2 for guiding the measuring light L1 to the rotary optical fiber FB1 and guiding the returning light L3 guided by the rotary optical fiber FB1; and the optical rotary adapter 18 for rotatably connecting the rotary optical fiber FB1 to the stationary optical fiber FB2 to transmit the measuring light L1 and the returning light L3.

The optical tomographic imaging system 10a further comprises in the main body of the system 11a the optical path length adjuster 26 for adjusting the optical path length of the reference light L2, a polarization controller 27a for rotating the polarization direction of the reference light L2 and a polarization controller 27b for rotating the polarization direction of the returning light L3, a circulator 25a for guiding the reference light L2 guided from the splitter 14a to the optical path length adjuster 26 and guiding optical path length adjusted reference light L2a guided from the optical path length adjuster 26 to the polarization controller 27a, a circulator 25b for guiding the measuring light L1 guided from the splitter 14a to the optical rotary adapter 18 and guiding the returning light L3 guided from the optical rotary adapter 18 to the polarization controller 27b, the first detector 30a for detecting a first reference light L4a produced by the combiner 14b and the second detector 30b for detecting a second interference light L4b produced by the combiner 14b, the operation control 32 for entering various conditions in the processor 22, the display 24, etc., and changing the settings, and the like.

As will be described later, the optical tomographic imaging system 10a illustrated in FIG. 8 uses various optical fibers FBs (e.g., FB2a, FB3, FB4a, FB4b, FB5, FB5a, F87, and FB8) including the rotary optical fiber FB1 and the stationary optical fiber FB2 to provide optical transmission paths for guiding and transmitting between components such as the optical devices as described earlier various light beams including the emitted light La, the measuring light L1, the reference light L2, the optical path length adjusted reference light L2a, the returning light L3, and the interference light L4a and L4b.

The splitter 14a, the combiner 14b, the interference light detector 20, the circulators 25a and 25b, the optical path length adjuster 26, the polarization controllers 27a and 27b, the detectors 30a and 30b and the above-mentioned optical fibers FBs (FB1 to FB8) make up an interferometer.

Next, the splitter 14a, the combiner 14b, the interference light detector 20, the circulators 25a and 25b, the optical path length adjuster 26, the polarization controllers 27a and 27b, and the detectors 30a and 30b constituting the interferometer will be described.

The splitter 14a is formed, for example, of a 2×2 optical fiber coupler and optically connected with the optical fibers FB3, FB2a and FB5a.

The splitter 14a splits the light La delivered from the light source unit 12 through the optical fiber FB3 into the measuring light L1 and the reference light L2, delivering the measuring light L1 to the circulator 25b through the optical fiber FB2a and the reference light L2 to the circulator 25a through the optical fiber FB5a.

The splitter 14b is formed, for example, of a 2×2 optical fiber coupler and optically connected with the optical fibers FB4a, FB4b, FB7 and FB8.

The splitter 14b combines the reference light L2a delivered from the polarization controller 27a through the optical fiber FB7 and the returning light L3 delivered from the polarization controller 27b through the optical fiber FB8 to produce the first interference light L4a and the second interference light L4b, delivering the first interference light L4a to the first detector 30a through the optical fiber FB4a and the second interference light L4b to the first detector 30b through the optical fiber FB4b.

The optical circulator 25a is connected with the optical fibers FB5, FB5a, and FB7, and transmits light guided through a given optical fiber to another given optical fiber. Specifically, the optical circulator 25a delivers the reference light L2 guided from the splitter 14a through the optical fiber FB5a to the optical path length adjuster 26 through the optical fiber FB5 and delivers the reference light L2a, which is guided through the optical fiber FB5 after it is reflected in the optical path length adjuster 26 to adjust its optical path length, to the polarization controller 27a through the optical fiber FB7.

The optical circulator 25b is connected with the optical fibers FB2, FB2a, and FB8, and transmits light guided through a given optical fiber to another given optical fiber. Specifically, the optical circulator 25b delivers the measuring light L1 guided from the splitter 14a through the optical fiber FB2a to the optical rotary adapter 18 through the optical fiber FB2 and transmits the returning light L3 guided from the optical rotary adapter 18 through the optical fiber FB2 to the polarization controller 27b through the optical fiber FB8.

The optical path length adjuster 26 is disposed on the side of the optical fiber FB5 from which the reference light L2 is emitted (that is, at the end of the optical fiber FB5 opposite from the splitter 14a).

The optical path length adjuster 26 adjusts the optical path length of the reference light L2 split by the splitter 14a and guided through the optical circulator 27a and the optical fiber FB5, and then emits and returns the optical path length adjusted reference light L2a to the optical circulator 27a through the optical fiber FB5.

The first detector 30a is optically connected with the combiner 14b through the optical fiber FB4a and detects the optical intensity of the first interference light L4a produced by the combiner 14b and guided through the optical fiber FB4a, outputting the results to the interference light detector 20. The second detector 30b is optically connected with the combiner 14b through the optical fiber FB4b and detects the optical intensity of the second interference light L4b produced by the combiner 14b and guided through the optical fiber FB4b, outputting the results to the interference light detector 20.

The polarization controller 27a is optically connected with the optical fiber FB7 and rotates the polarization direction of the reference light L2a. The polarization controller 27b is optically connected with the optical fiber FB8 and rotates the polarization direction of the returning light L3.

The polarization controller 27a and the polarization controller 27b may be configured using known technology such as is disclosed, for example, in JP 2001-264246 A.

Adjusting the polarization direction of the returning light L3 and the reference light L2a in the polarization controllers 27a and 27b prior to combining them in the combiner 14b allows the combiner 14b to combine the returning light L3 and the reference light L2a of which the respective polarization directions have been adjusted to coincide, yielding a further sharpened tomographic image.

The polarization controllers 27a and 27b preferably permit operation thereof by a medical person at the operation control.

The interference light detector 20 is connected with the detectors 30a and 30b through the optical fibers FB4a and FB4b, respectively, and detects (or generates) the interference signal from the difference between the first interference light L4a passed through the first detector 30a and the second interference light L4b passed through the second detector 30b.

Specifically, the interference light detector 20 is composed of a detecting unit formed by, for example, a photodiode for detecting the interference light by photoelectric conversion and a differential amplifier for detecting the difference from the value detected by the detecting unit; the interference light detector 20 effects photoelectric conversion of the first interference light L4a and the second interference light L4b in the detecting unit, enters the detected value in the differential amplifier 73 and amplifies the difference in the differential amplifier 73 to produce the interference signal.

Thus, performing balance detection of the two beams of interference light, the first interference light L4a and the second interference light L4b, permits producing an amplified interference signal while removing the common-mode optical noise from the interference signal, which enables improvement of the image quality of the acquired tomographic image.

According to the detection results given by the detectors 30a and 30b, the interference light detector 20 adjusts the balance between the first interference light L4a and the second interference light L4b in the optical intensity with which detection is made.

Thus, adjusting the balance of the optical intensity between the first interference light L4a and the second interference light L4b according to the detection results given by the detectors 30a and 30b or, specifically, adjusting the optical intensity to 50:50 permits reducing the white noise component and increasing the signal-to-noise ratio.

As described above, the optical tomographic imaging system 10a illustrated in FIG. 8 is also capable of efficiently acquiring high-resolution optical tomographic image of the object under measurement as is the optical tomographic imaging system 10 illustrated in FIG. 1.

While the optical tomographic imaging systems 10 and 10a described above uses SS-OCT (swept source-OCT) measuring method to detect the contact area with the object under measurement and thereby acquire a tomographic image of the object under measurement, the invention is not limited in this way and may use any other OCT measuring method. The other OCT measuring methods that may be used here include, for example, an SD-OCT (spectral domain-OCT) measuring method and a TD-OCT (time domain-OCT) measuring method.

While the optical rotary adapter of the invention and the optical tomographic imaging system using the same have been described in detail by reference to various embodiments thereof, the present invention is not limited in any manner to these embodiments, and various improvements and modifications may be made without departing from the spirit of the invention.

For example, while the fixed sleeve and the rotary assembly of the optical rotary adapter are provided each in a one-piece configuration in the above embodiments, any other configuration may be used, provided that the rotary optical transmission system composed of the rotary optical fiber and the rotary collimating lens can be integrally provided and the stationary optical transmission system composed of the stationary optical fiber and the stationary collimating lens can be integrally provided, that the rotary optical transmission system can be rotatably supported with respect to the stationary optical transmission system, and that the central axes of the rotary optical fiber and the stationary optical fiber are offset from the center of rotation (e.g., the center of rotation of the rotary assembly, i.e., the mounting cylinder and the rotary cylinder) by a given amount to lessen the attenuation of the returning light from the object under measurement, reduce white noise and improve the signal-to-noise ratio of the returning light. For example, the composite parts of the fixed sleeve, the mounting cylinder and the rotary cylinder of the rotary assembly, and the connecting unit, such as the discal section, the circular tubing section, and cylindrical sections may be provided as discrete component parts. Further, any configuration may be used provided that the rotary optical transmission system can be rotatably and removably supported with respect to the stationary optical transmission system.

What is claimed is:

1. An optical rotary adapter used with an optical tomographic imaging system for acquiring an optical tomogaphic image of an object under measurement, said optical rotary adapter rotatably connecting optical fibers guiding measuring light to said object under measurement and guiding reflected returning light from said object under measurement, said optical rotary adapter comprising:
   a fixed sleeve,
   a stationary optical fiber fixedly supported by said fixed sleeve and having on one end thereof an inclined end face inclined a given angle with respect to a plane perpendicular to a central axis of said stationary optical fiber,
   a stationary collimating lens spaced a given distance from said inclined end face of said optical fiber,
   a mounting cylinder carried rotatably with respect to said fixed sleeve,
   a rotary optical fiber fixedly mounted to said mounting cylinder so as to be disposed opposite said stationary collimating lens and having an inclined end face inclined a given angle with respect to a plane perpendicular to a central axis of said rotary optical fiber,
   a rotary collimating lens fixedly mounted to said mounting cylinder and disposed between said stationary collimating lens and said rotary optical fiber with a given distance from said inclined end face of said rotary optical fiber, and
   rotation actuating means for rotating said mounting cylinder,
   wherein said central axes of said stationary optical fiber and said rotary optical fiber are offset from or inclined with respect to a central axis of rotation of said mounting cylinder to reduce attenuation of said returning light.

2. The optical rotary adapter according to claim 1, wherein said stationary optical fiber is fixedly supported substantially at a center of said fixed sleeve whereas said rotary optical fiber is fixedly supported substantially at a center of said mounting cylinder such that said central axes of said stationary optical fiber and said rotary optical fiber are parallel to and offset from said central axis of rotation of said mounting cylinder to reduce attenuation of said returning light.

3. The optical rotary adapter according to claim 1, wherein respective offset amounts $\delta 1$ and $\delta 2$ between said central axes of said stationary optical fiber and said rotary optical fiber with respect to said central axis of rotation of said mounting cylinder satisfy following expressions (1), (2), (3) and (4):

$$n1 \times \sin\theta 1 = n3 \times \sin\theta 3 \quad (1)$$

$$\delta 1 = f1 \times \tan(\theta 3 - \theta 1) \quad (2)$$

$$n2 \times \sin\theta 2 = n3 \times \sin\theta 4 \quad (3)$$

$$\delta 2 = f2 \times \tan(\theta 4 - \theta 2) \quad (4)$$

where $\theta 1$ and $\theta 2$ are—inclination angles respectively of said inclined end faces of said stationary optical fiber and said rotary optical fiber with respect to planes perpendicular to the central axes of said optical fibers; n1 and n2 are refractive indices respectively of said stationary optical fiber and said rotary optical fiber; n3 is refractive index of a medium between said stationary optical fiber and said rotary optical fiber propagating light; $\theta 3$ and $\theta 4$ are angles of light traveling inside said optical fibers in a direction parallel to said central axes of said optical fibers and refracted at interfaces between said inclined end faces of said optical fibers and said medium with respect to respective normal lines to said inclined end faces; and f1 and f2 are focal distances, respectively, of said stationary collimating lens and said rotary collimating lens, said focal distances being equal respectively to distances along the optical axes between respective centers of the inclined end faces of said stationary optical fiber and said rotary optical fiber on the one hand and respective centers of said stationary collimating lens and said rotary collimating lens on the other hand assuming that said collimating lenses are thin sheet lenses.

4. The optical rotary adapter according to claim 1, wherein said stationary optical fiber and said rotary optical fiber are supported by ferrules, respectively, and said ferrules have their respective inclined end faces sharing same planes respectively with said inclined end faces of said stationary optical fiber and said rotary optical fiber.

5. The optical rotary adapter according to claim 4, wherein said stationary optical fiber and said rotary optical fiber are supported at the center of their respective ferrules held by respective holders fixedly mounted to said fixed sleeve and said mounting cylinder, respectively, such that said central axes of said stationary optical fiber and said rotary optical fiber are in an offset position from said central axis of rotation of said mounting cylinder by offsetting said ferrules respectively supporting said stationary optical fiber and said rotary optical fiber.

6. The optical rotary adapter according to claim 1, wherein said stationary optical fiber and said rotary optical fiber are disposed such that said centers of their respective inclined end faces lie on said central axis of rotation, wherein said stationary collimating lens and said rotary collimating lens are disposed such that their respective centers lie on said central axis of rotation, wherein said stationary optical fiber is fixedly supported by said fixed sleeve at a given inclination angle while said rotary optical fiber is fixedly mounted to said mounting cylinder at a given inclination angle, and wherein said central axes of said stationary optical fiber and said rotary optical fiber are each inclined with respect to said central axis of rotation of said mounting cylinder to reduce attenuation of said returning light.

7. The optical rotary adapter according to claim 1, wherein inclination angles $\phi 1$ and $\phi 2$ between said central axes of said stationary optical fiber and said rotary optical fiber, respectively, with respect to said central axis of rotation of said mounting cylinder satisfy following expressions (5), (6), (7) and (8):

$$n1 \times \sin\theta1 = n3 \times \sin\theta3 \quad (5)$$

$$\phi1 = \theta3 = -\theta1 \quad (6)$$

$$n2 \times \sin\theta2 = n3 \times \sin\theta4 \quad (7)$$

$$\phi2 = \theta4 - \theta2 \quad (8)$$

where $\theta1$ and $\theta2$ are inclination angles of said inclined end faces of the stationary optical fiber and the rotary optical fiber, respectively, with respect to planes perpendicular to the central axes of said optical fibers; n1 and n2 are refractive indices, respectively, of said stationary optical fiber and said rotary optical fiber; n3 is refractive index of a medium between said stationary optical fiber and said rotary optical fiber propagating light; and $\theta3$ and $\theta4$ are angles of light traveling inside said optical fibers in a direction parallel to said central axes of said optical fibers and refracted at interfaces respectively between said inclined end faces of said optical fibers and said medium with respect to normal lines to the respective end faces of said stationary optical fiber and said rotary optical fiber.

8. The optical rotary adapter according to claim 1, wherein said stationary optical fiber and said rotary optical fiber are supported by ferrules, respectively, and said ferrules have their respective inclined end faces sharing same planes respectively with said inclined end faces of said stationary optical fiber and said rotary optical fiber.

9. The optical rotary adapter according to claim 8, wherein said stationary optical fiber and said rotary optical fiber are supported at the center of their respective ferrules held by respective holders fixedly mounted to said fixed sleeve and said mounting cylinder, respectively, such that said central axes of said stationary optical fiber and said rotary optical fiber are inclined with respect to said central axis of rotation of said mounting cylinder by inclining said ferrules supporting said stationary optical fiber and said rotary optical fiber, respectively.

10. The optical rotary adapter according to claim 1, wherein said stationary optical fiber and said stationary collimating lens on the one hand and said rotary optical fiber and said rotary collimating lens on the other hand are disposed so as to become symmetric as said rotary optical fiber and said rotary collimating lens rotate.

11. The optical rotary adapter according to claim 1, wherein said mounting cylinder fixedly supporting said rotary optical fiber and said rotary collimating lens are removable from said fixed sleeve fixedly supporting said rotary optical fiber and said rotary collimating lens.

12. The optical rotary adapter according to claim 1, further comprising:
a rotary cylinder having one end thereof attached to said mounting cylinder and rotating about said central axis of rotation unitarily with said mounting cylinder,
wherein said inclined end face of one end of said rotary optical fiber is attached to said mounting cylinder such that the central axis of said rotary optical fiber is offset or inclined with respect to said central axis of rotation of said mounting cylinder, and
said rotary optical fiber is supported by said rotary cylinder at the other end of said rotary cylinder.

13. The optical rotary adapter according to claim 12, wherein said rotary optical fiber is supported at the other end of said rotary cylinder at a center of said rotary cylinder such that said central axis of said rotary optical fiber coincides with said central axis of rotation of said mounting cylinder.

14. The optical rotary adapter according to claim 12, wherein said rotary optical fiber has the other end face at said other end of said rotary cylinder, said other end of said rotary cylinder forming a terminal for a fixed type optical connector.

15. The optical rotary adapter according to claim 14, wherein the other end face of said rotary optical fiber is supported at a center of said rotary cylinder such that said central axis of said rotary optical fiber coincides with said central axis of rotation of said mounting cylinder.

16. The optical rotary adapter according to claim 12, wherein said rotary optical fiber extends from said other end of said rotary cylinder and has a tip connected to a measuring unit for irradiating said object under measurement with said measuring light and acquiring returning light from said object under measurement, said rotary optical fiber being rotatably held in a transparent probe sheath to form part of an optical probe.

17. An optical tomographic imaging system comprising:
a main body of system for acquiring an optical tomographic image of an object under measuring;
an optical probe including a rotary optical fiber for guiding measuring light from said main body of the system to said object under measurement and guiding returning light from said object under measurement, a measuring unit disposed at a tip of said rotary optical fiber for irradiating said object under measurement with said measuring light and acquiring returning light from said object under measurement, and a probe sheath covering the periphery of said rotary optical fiber and said measuring unit so as to rotatably hold said rotary optical fiber and said measuring unit and having at least a region thereof formed of a transparent material transmitting said measuring light from said measuring unit and said returning light from said object under measurement;
a stationary optical fiber connected with said main body of the system for guiding said measuring light to said rotary optical fiber and guiding said returning light guided by said rotary optical fiber to said main body of the system; and
the optical rotary adapter according to claim 1 for rotatably connecting said rotary optical fiber to said stationary optical fiber to transmit said measuring light and said returning light,
wherein said main body of the system uses said guided returning light to acquire said optical tomographic image of said object under measurement.

18. The optical tomographic imaging system according to claim 17, wherein said main body of the system comprises:
a light source;
a splitter for splitting light emitted from said light source into said measuring light and reference light;
a combiner for combining said returning light detected by said measuring unit of said optical probe and guided through said rotary optical fiber, said optical rotary adapter and said stationary optical fiber with said reference light to generate interference light;
an interference light detector for detecting said interference light as interference signal; and
a tomographic information generator for acquiring said tomographic image from said interference signal detected by said interference light detector.

19. The optical tomographic imaging system according to claim 18, wherein said light source emits light as it sweeps a wavelength with a constant period.

* * * * *